(12) United States Patent
Wang et al.

(10) Patent No.: US 12,240,849 B2
(45) Date of Patent: Mar. 4, 2025

(54) NITROGEN-CONTAINING SPIRO DERIVATIVE AS RET INHIBITOR

(71) Applicant: GUANGZHOU BAIYUNSHAN PHARMACEUTICAL HOLDINGS CO., LTD. BAIYUNSHAN PHARMACEUTICAL GENERAL FACTORY, Guangdong (CN)

(72) Inventors: Jiansong Wang, Guangdong (CN); Zhifei Fu, Shanghai (CN); Zhibo Luo, Guangdong (CN); Miaorong Luo, Shanghai (CN); Yang Zhang, Shanghai (CN); Yalei Cai, Shanghai (CN); Wu Zhu, Shanghai (CN); Jian Li, Shanghai (CN); Shuhui Chen, Shanghai (CN); Yingxia Bao, Guangdong (CN); Wei Wang, Guangdong (CN); Zhoufan Xie, Guangdong (CN)

(73) Assignee: GUANGZHOU BAIYUNSHAN PHARMACEUTICAL HOLDINGS CO., LTD. BAIYUNSHAN PHARMACEUTICAL GENERAL FACTORY, Guangdong (CN)

( * ) Notice: Subject to any disclaimer, the term of this patent is extended or adjusted under 35 U.S.C. 154(b) by 754 days.

(21) Appl. No.: 17/600,994

(22) PCT Filed: Apr. 3, 2020

(86) PCT No.: PCT/CN2020/083255
§ 371 (c)(1),
(2) Date: Oct. 1, 2021

(87) PCT Pub. No.: WO2020/200314
PCT Pub. Date: Oct. 8, 2020

(65) Prior Publication Data
US 2022/0204507 A1    Jun. 30, 2022

(30) Foreign Application Priority Data

Apr. 3, 2019   (CN) .......................... 201910270287.2
Sep. 29, 2019  (CN) .......................... 201910937884.6
Oct. 15, 2019  (CN) .......................... 201910980684.9
Mar. 19, 2020  (CN) .......................... 202010199443.3

(51) Int. Cl.
*C07D 471/10*   (2006.01)
*A61P 35/00*    (2006.01)
*C07D 401/14*   (2006.01)
*C07D 413/14*   (2006.01)
*C07D 498/10*   (2006.01)

(52) U.S. Cl.
CPC ............ *C07D 471/10* (2013.01); *A61P 35/00* (2018.01); *C07D 401/14* (2013.01); *C07D 413/14* (2013.01); *C07D 498/10* (2013.01)

(58) Field of Classification Search
CPC ................ C07D 471/10; C07D 401/14; C07D 413/14; C07D 498/10; A61P 35/00
See application file for complete search history.

(56) References Cited

FOREIGN PATENT DOCUMENTS

| WO | 2016/127074 A1 | 8/2016 |
|----|----------------|--------|
| WO | 2017/079140 A1 | 5/2017 |
| WO | 2017/161269 A1 | 9/2017 |
| WO | 2018/017983 A1 | 1/2018 |
| WO | 2018/022761 A1 | 2/2018 |
| WO | 2018/136663 A1 | 7/2018 |

OTHER PUBLICATIONS

International Search Report issued to International Application No. PCT/CN2020/083255, with a date of mailing of Jun. 23, 2020 (in Chinese and English translation).
Written Opinion issued to International Application No. PCT/CN2020/083255, with a date of mailing of Jun. 23, 2020 (in Chinese and English translation).

*Primary Examiner* — Rayna Rodriguez
*Assistant Examiner* — W. Justin Youngblood
(74) *Attorney, Agent, or Firm* — Hoffmann & Baron, LLP

(57) ABSTRACT

Disclosed are a series of compounds with a nitrogen-containing spiro structure and an application thereof in the preparation of an RET kinase inhibitor. Specifically, disclosed is a compound as shown in formula (II) or a pharmaceutically acceptable salt thereof.

(II)

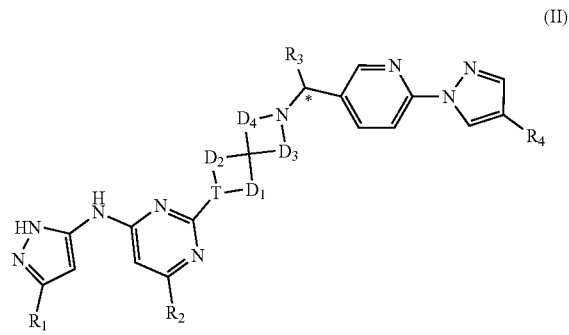

19 Claims, No Drawings

NITROGEN-CONTAINING SPIRO DERIVATIVE AS RET INHIBITOR

CROSS-REFERENCE TO RELATED APPLICATIONS

The present application is a national phase entry under 35 USC § 371 of International Application PCT/CN2020/083255, filed Apr. 3, 2020, which claims the benefits of the following priorities:
CN201910270287.2, the filing date is Apr. 3, 2019;
CN201910937884.6, the filing date is Sep. 29, 2019;
CN201910980684.9, the filing date is Oct. 15, 2019;
CN202010199443.3, the filing date is Mar. 19, 2020;
the entire disclosures of which are incorporated herein by reference.

TECHNICAL FIELD

The present disclosure relates to a series of compounds with a nitrogen-containing spiro structure and uses thereof in the preparation of a RET kinase inhibitor. Specifically, the present disclosure relates to compounds of formula (1) and formula (II) or pharmaceutically acceptable salts thereof.

BACKGROUND

A RET protein is a receptor tyrosine kinase (RTK), and is also a transmembrane glycoprotein meanwhile. The RET protein is expressed by a proto-oncogene RET (Rearranged during Transfection), and plays an important role in development of kidney and enteric nervous systems at embryo stage. In addition, the homeostasis of RET protein is crucial in a variety of tissues, such as nerve cells, neuroendocrine cells, hemopotietic tissues and male germ cells. Different from other RTK, RET does not directly bind to ligand molecules, such as GDNF family of ligands (GFLs), including neurodirectin (artemin), glial cell-derived neurotrophic factor (GDNF), neurturin and persephin. These GFLs typically bind to GDNF family receptor α (GFRα) to form GFLs-GFRα composite, which mediates self-dimerization of the RET protein, causes trans-self-phosphorylation reaction of tyrosine in an intracellular domain, recruits relevant linker proteins, and activates signaling cascade reaction such as cell proliferation. Relevant signaling pathways include MAPK, PI3K, JAK-STAT, PKA, PKC and the like.

There are two main carcinogenic activation mechanisms of RET: one mechanism is that rearrangement of chromosome generates new fusion proteins, generally including a kinase domain of RET and a fusion protein containing a self-dimerization domain; the other mechanism is that mutation of RET directly or indirectly activates the kinase activity of RET. Change in the level of these somatic cells or germ cells involves pathogenesis of multiple cancers. RET chromosome rearrangement is found in 5%-10% of patients suffering from papillary thyroid carcinoma; RET point mutation is found in 60% of patients suffering from medullary thyroid medullary carcinoma; about 1%-2% of the non-small-cell lung cancer (NSCLC) patients have RET fusion proteins, in which KIF5B-RET is most common.

To summarize, abnormal RET expression or activation is found in multiple tumors and gastrointestinal tract disorders such as allergic bowel syndrome. Thus, RET inhibitors have potential clinical value in tumors and gastrointestinal tract disorder diseases.

SUMMARY

The present disclosure provides a compound of formula (I), an isomer or a pharmaceutically acceptable salt thereof.

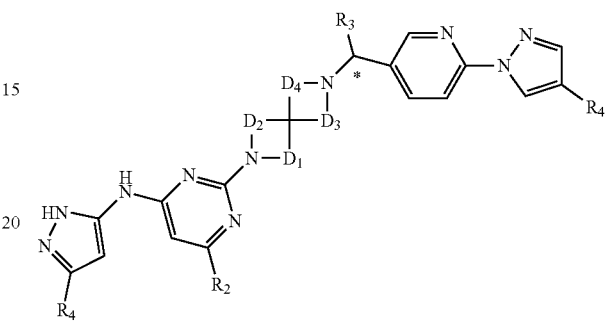

wherein,
$R_1$ is selected from H, F, Cl, Br, I and $C_{1-6}$ alkyl, and the $C_{1-6}$ alkyl is optionally substituted with 1, 2 or 3 $R_a$;
$R_2$ is selected from H, F, Cl, Br, I and $C_{1-6}$ alkyl, and the $C_{1-6}$ alkyl is optionally substituted with 1, 2 or 3 $R_b$;
$R_3$ is selected from H, F, Cl, Br, I and $C_{1-6}$ alkyl, and the $C_{1-6}$ alkyl is optionally substituted with 1, 2 or 3 $R_c$;
$R_4$ is selected from H, F, Cl, Br, I, OH, $NH_2$ and $C_{1-3}$ alkyl, and the $C_{1-3}$ alkyl is optionally substituted with 1, 2 or 3 $R_d$;
$D_1$ is —$CH_2CH_2$— optionally substituted with 1, 2 or 3 $R_e$;
$D_2$ is —$CH_2CH_2$— optionally substituted with 1, 2 or 3 $R_f$;
$D_3$ is selected from —$CH_2$— and

and the —$CH_2$— is optionally substituted with 1 or 2 $R_g$;
$D_4$ is selected from —$CH_2CH_2$— and —$CH_2CH_2CH_2$—, each of which is optionally substituted with 1, 2 or 3 $R_h$;
$R_a$, $R_b$, $R_c$ and $R_d$ are independently selected from F, Cl, Br, I, OH, $NH_2$ and $CH_3$;
$R_e$, $R_f$, $R_g$ and $R_h$ are independently selected from F, Cl, Br, I and $CH_3$;
a carbon atom with "*" is a chiral carbon atom, which is present in a form of (R) or (S) single enantiomer or in an enriched enantiomeric form.

The present disclosure also provides a compound of formula (II) or a pharmaceutically acceptable salt thereof, (II)

wherein,

T is selected from CH and N;

$R_1$ is selected from H, F, Cl, Br, I and $C_{1-6}$ alkyl, and the $C_{1-6}$ alkyl is optionally substituted with 1, 2 or 3 $R_a$;

$R_2$ is selected from H, F, Cl, Br, I and $C_{1-6}$ alkyl, and the $C_{1-6}$ alkyl is optionally substituted with 1, 2 or 3 Rn;

$R_3$ is selected from H, F, Cl, Br, I and $C_{1-6}$ alkyl, and the $C_{1-6}$ alkyl is optionally substituted with 1, 2 or 3 $R_c$;

$R_4$ is selected from H, F, Cl, Br, I, OH, $NH_2$ and $C_{1-3}$ alkyl, and the $C_{1-3}$ alkyl is optionally substituted with 1, 2 or 3 $R_d$;

$D_1$ is —$CH_2CH_2$— optionally substituted with 1, 2 or 3 $R_e$;

$D_2$ is —$CH_2CH_2$— optionally substituted with 1, 2 or 3 $R_f$;

$D_3$ is selected from —$CH_2$— and

<image> and the —$CH_2$— is optionally substituted with 1 or 2 $R_g$;

$D_4$ is selected from —$CH_2CH_2$—, —$CH_2CH_2CH_2$— and —O—$CH_2CH_2$—, each of which is optionally substituted with 1, 2 or 3 $R_h$;

$R_a$, $R_b$, $R_c$ and $R_d$ are independently selected from F, Cl, Br, I, OH, $NH_2$ and $CH_3$;

$R_e$, $R_f$, $R_g$ and $R_h$ are independently selected from F, Cl, Br, I and $CH_3$;

a carbon atom with "*" is a chiral carbon atom, which is present in a form of (R) or (S) single enantiomer or an enriched enantiomeric form.

In some embodiments of the present disclosure, in the compound, isomer or pharmaceutically acceptable salt thereof, wherein $R_1$ is selected from H, F, Cl, Br, I, $CH_3$, $CH_2CH_3$, <image> and the $CH_3$, $CH_2CH_3$,

<image> are optionally substituted with 1, 2 or 3 $R_a$, and other variables are as defined herein.

In some embodiments of the present disclosure, $R_1$ is selected from H, F, Cl, Br, I, $CH_3$, $CF_3$, $CH_2CH_3$, $CH_2CF_3$, <image> and other variables are as defined herein.

In some embodiments of the present disclosure, $R_1$ is $CH_3$, and other variables are as defined herein.

In some embodiments of the present disclosure, $R_2$ is selected from H, F, Cl, Br, I, $CH_3$, $CH_2CH_3$, <image> wherein $CH_3$, $CH_2CH_3$,

<image> are optionally substituted with 1, 2 or 3 $R_b$, and other variables are as defined herein.

In some embodiments of the present disclosure, $R_2$ is selected from H, F, Cl, Br, I, $CH_3$, $CF_3$, $CH_2CH_3$, $CH_2CF_3$, <image> and other variables are as defined herein.

In some embodiments of the present disclosure, $R_2$ is $CH_3$, and other variables are as defined herein.

In some embodiments of the present disclosure, $R_3$ is selected from H, F, Cl, Br, I, $CH_3$, $CH_2CH_3$, <image> wherein $CH_3$, $CH_2CH_3$,

<image> and are optionally substituted with 1, 2 or 3 $R_c$, and other variables are as defined herein.

In some embodiments of the present disclosure, $R_3$ is selected from H, F, Cl, Br, I, $CH_3$, $CF_3$, $CH_2CH_3$, $CH_2CF_3$,

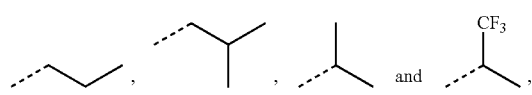

and other variables are as defined herein.

In some embodiments of the present disclosure, $R_3$ is $CH_3$, and other variables are as defined herein.

In some embodiments of the present disclosure, $R_4$ is selected from H, F, Cl, Br, I, $CH_3$, $CF_3$, $CH_2CH_3$, $CH_2CF_3$,

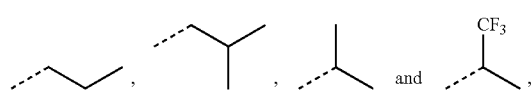

and other variables are as defined herein.

In some embodiments of the present disclosure, $R_4$ is F, and other variables are as defined herein.

In some embodiments of the present disclosure, the structure unit

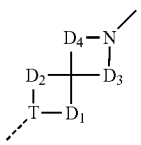

is selected from

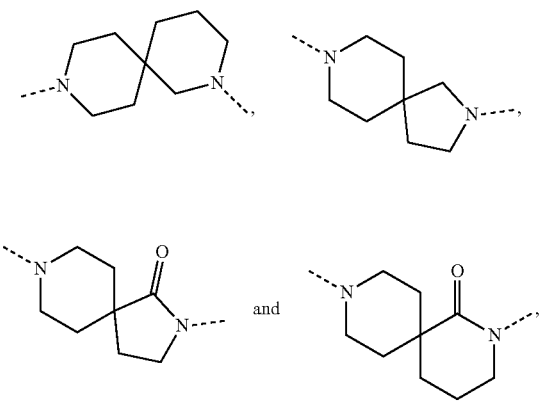

and other variables are as defined herein.

In some embodiments of the present disclosure, the structure unit

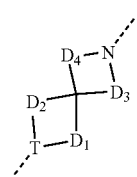

is selected from

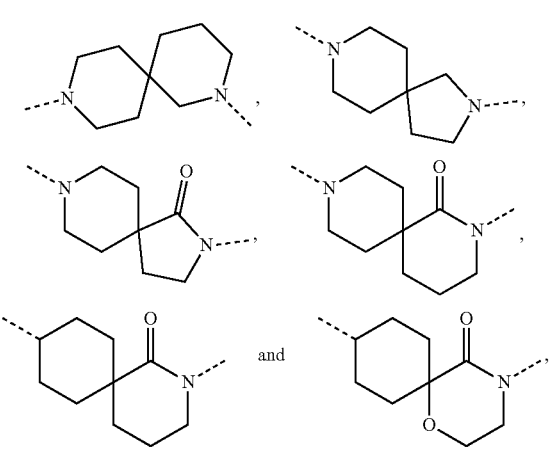

and other variables are as defined herein.

In some embodiments of the present disclosure, the structure unit

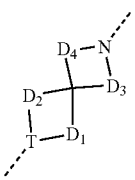

is selected from

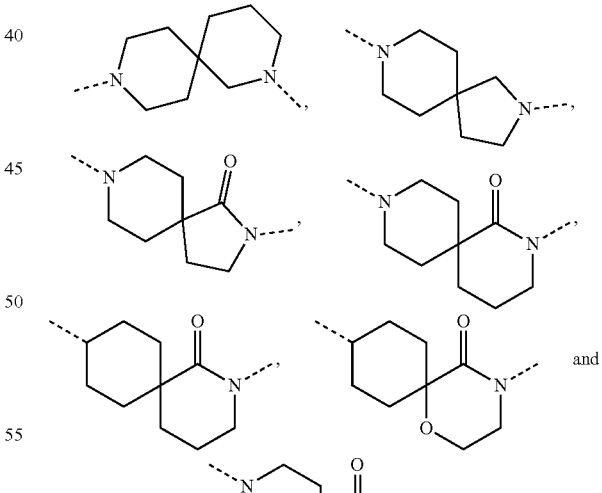

and other variables are as defined herein.

In some embodiments of the present disclosure, the compound or pharmaceutically acceptable salt thereof is selected from

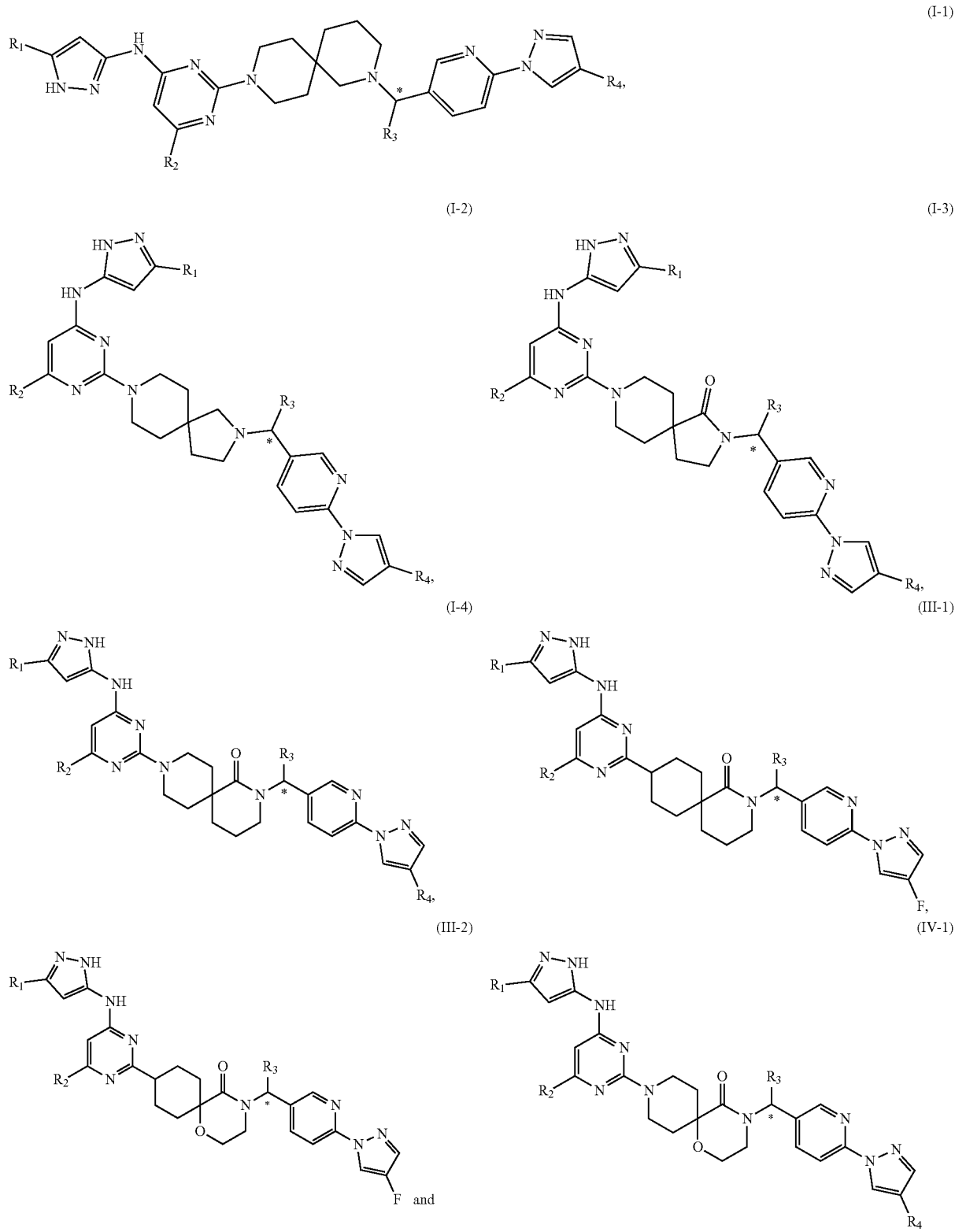

wherein, R₁, R₂, R₃ and R₄ are as defined herein.

a carbon atom with "*" is a chiral carbon atom, which is present in a form of (R) or (S) single enantiomer or in an enriched enantiomeric form.

The present disclosure also provides some embodiments which are formed by any combinations of above variables.

The present disclosure also provides a compound as shown in the following formula, an isomer or a pharmaceutically acceptable salt thereof:

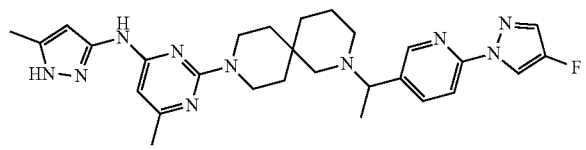
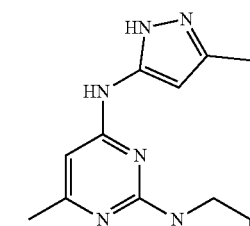
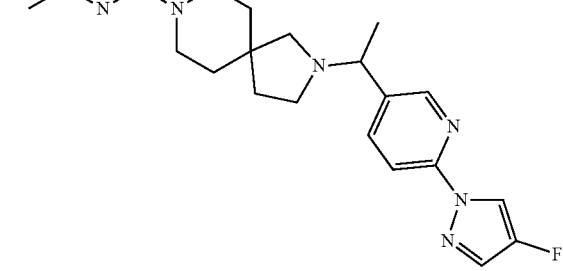
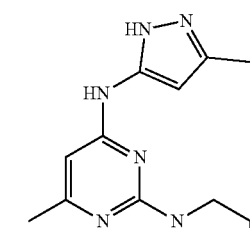
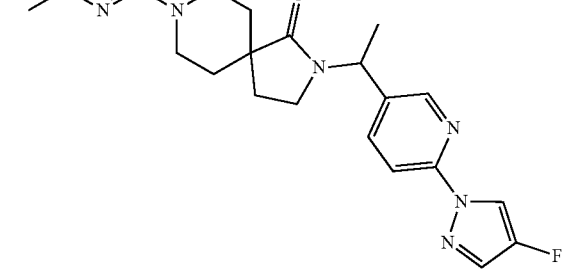
The present disclosure also provides a compound as shown in the following formula or a pharmaceutically acceptable salt thereof:
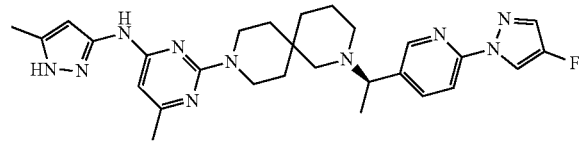
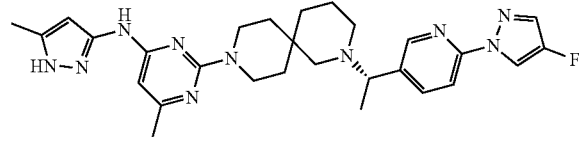

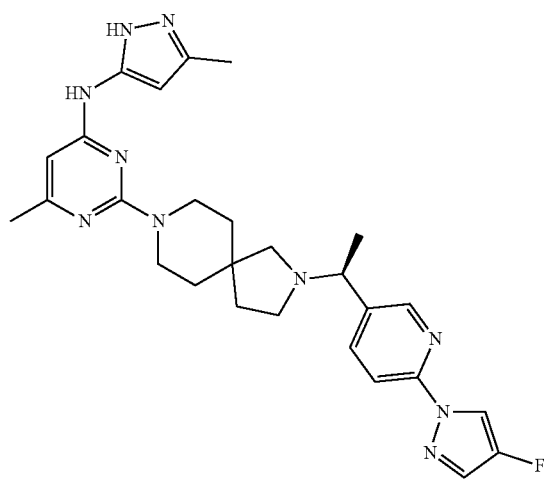
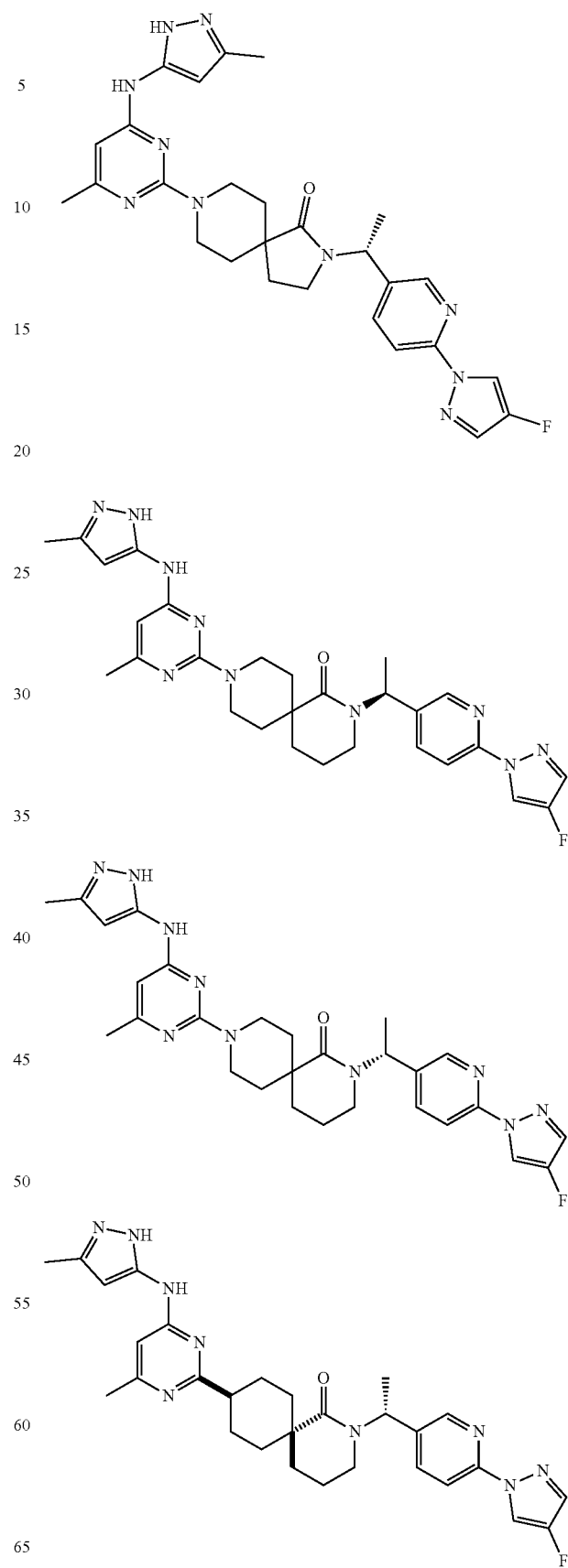

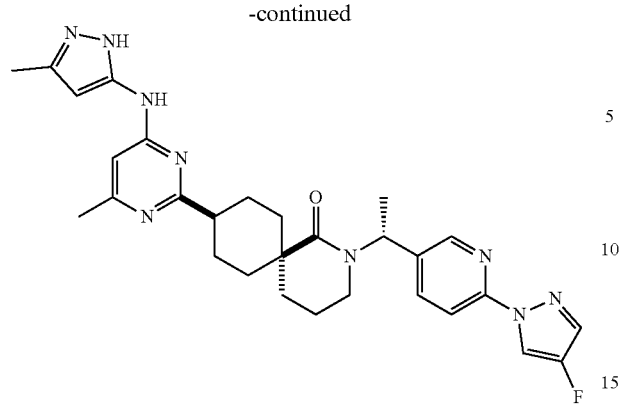
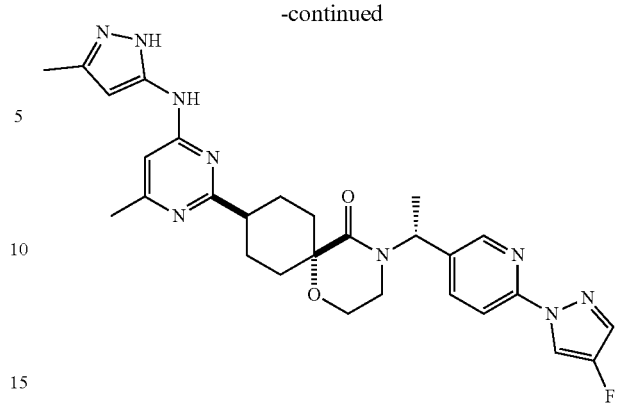
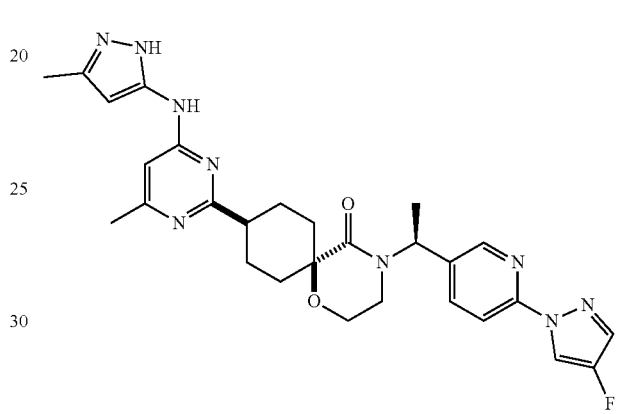
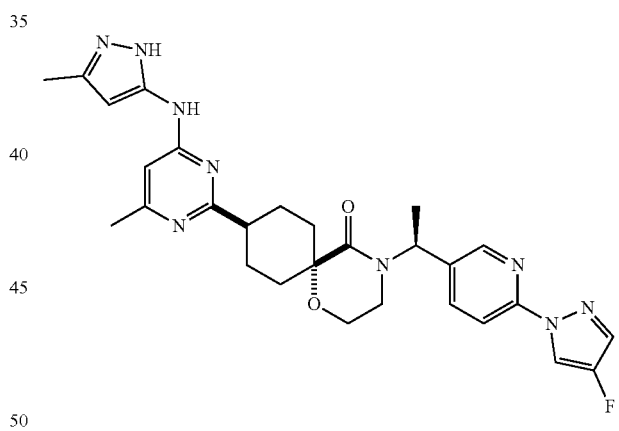
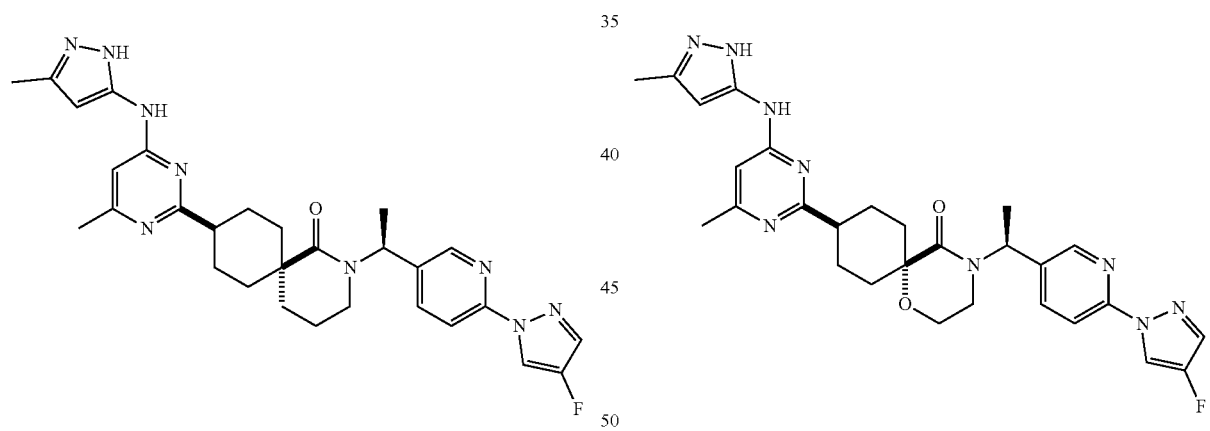
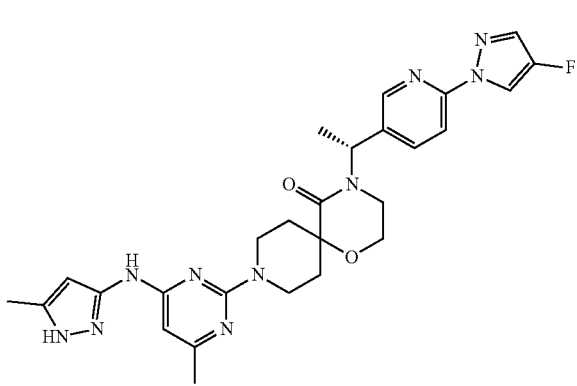

-continued

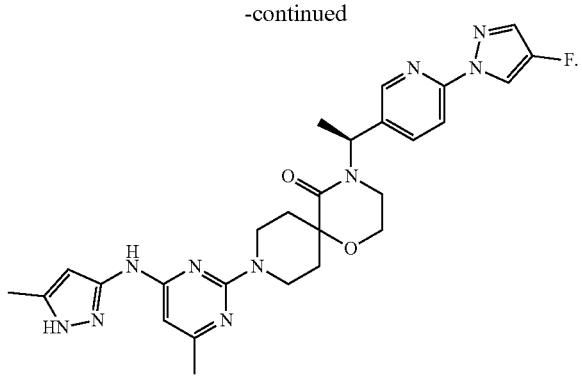

The present disclosure also provides a pharmaceutical composition, comprising a therapeutically effective amount of the above compound, an isomer or a pharmaceutically acceptable salt thereof, and a pharmaceutically acceptable carrier.

The present disclosure also provides use of the above compound, an isomer or a pharmaceutically acceptable salt thereof or the above composition in preparation of a RET kinase inhibitor.

Definition and Illustration

Unless otherwise stated, the following terms and phrases used herein are intended to have the following meanings. A specific term or phrase should not be considered indefinite or unclear without particular definitions, and should be understood according to common meanings. The trade names herein denote its corresponding goods or its active ingredient.

The term "pharmaceutically acceptable" used herein means that compounds, materials, compositions and/or dosage forms are suitable for use in contact with human and animal tissues within the scope of reliable medical judgment, without excessive toxicity, irritation, allergic reactions or other problems or complications, and commensurate with a reasonable benefit/risk ratio.

The term "pharmaceutically acceptable salt" refers to a salt of a compound of the present disclosure, which is prepared from a compound having a specific substituent of the present disclosure and relatively non-toxic acid or alkali. When the compound of the present disclosure contains relatively acidic function groups, an alkali addition salt can be obtained by contacting an enough amount of alkali with neutral forms of such compounds in a pure solution or an appropriate inert solvent. The pharmaceutically acceptable alkali addition salts include salts of sodium, potassium, calcium, ammonium, organic amine or magnesium, or similar salts. When the compound of the disclosure contains relatively alkaline functional groups, an acid addition salt can be obtained by contacting an enough amount of acids with neutral forms of such compounds in a pure solution or an appropriate inert solvent. Examples of pharmaceutically acceptable acid addition salts include inorganic acid salts, for example hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid, and the like; and organic acid salts, including for example similar I acids such as acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid and methanesulfonic acid, and the like; also include salts of amino acid (such as arginine); and salts of organic acids such as glucuronic acid. Some particular compounds of the present disclosure contain alkaline and acidic functional groups, so as to be converted into any one alkali or acid addition salt.

The pharmaceutically acceptable salt of the present disclosure can be synthesized by parent compounds containing acid radicals or alkaline groups using a conventional chemical method. In general, the preparation method of such salt is as follows: reacting the compounds having free acidic or alkaline form with stoichiometric appropriate alkalis or acids in water or an organic solvent or a mixture of both.

The structure of the compound of the present disclosure can be confirmed by conventional methods known by those skilled in the art. If the present disclosure relates to an absolute configuration of a compound, the absolute configuration can be confirmed by conventional technical means in the art. For example single crystal X-ray diffraction (SXRD), the diffraction intensity data of cultured single crystal is collected by a Bruker D8 venture diffraction instrument, the light source is CuKα radiation, the scanning manner is φ/ω scanning, and after relevant data is collected, the crystal structure is analyzed using a direct method (Shelxs97) so as to confirm the absolute configuration.

The compound of the present disclosure can have particular geometric or stereoisomer forms. In the present disclosure, it is conceived that all of these compounds include cis and trans isomers, (−)- and (+)-enantiomers, (R)- and (S)-enantiomers, diastereomers, (D)-isomers, (L)-isomers, and their racemic mixtures and other mixtures, for example an enriched mixture of enantiomers or diastereomers, all of these mixtures fall into the scope of the present disclosure. Substituents such as alkyl can have additional unsymmetrical carbon atoms. All of these isomers and their mixtures are all included within the scope of the present disclosure.

Unless otherwise stated, the term "enantomers" or "optical isomers" refer to stereoisomers which are in a mutual mirror-image relation.

Unless otherwise stated, the term "cis-trans-isomer" or "geometrical isomer" is caused by a fact that a double bond or a ring-forming carbon atom single bond cannot freely rotate.

Unless otherwise stated, the term "diastereoisomer" refers to a stereoisomer in which the molecule has two or more chiral centers, and the relationship between the molecules is non-mirror image.

Unless otherwise stated, "(D)" or "(+) represents dextrorotation, "(L)" or "(−) represents levorotation, "(DL)" or "(±)" represents racemization.

Unless otherwise stated, a wedge-shaped solid line bond (╱) and a wedge-shaped dashed line bond (⋰) are used to represent the absolute configuration of the stereocenter; a straight solid line bond (╱) and a straight dashed line bond (⋰) are used to represent the relative configuration of the stereocenter; and a wavy line (∿) is used to represent a wedge-shaped solid line bond (╱) or a wedge-shaped dashed line bond (⋰), or the wavy line (∿) is used to represent the straight solid line bond (╱) and the straight dashed line bond (⋰).

The compound of the present disclosure may exist in a specific form. Unless otherwise stated, the term "tautomer" or "tautomer form" means that different functional isomers are in dynamic balance at room temperature and can be rapidly transformed mutually. If the tautomer is possible (for example, in solution), the chemical balance of the tautomer can be achieved. For example, a proton tautomer (also referred as prototropic tautomer) includes mutual transformation via proton migration, such as keto-enol isomerization and imine-enamine isomerization. A valence tautomer includes mutual transformation performed by recombination of some bonding electrons. The specific example of the keto-enol isomerization is mutual transformation between two tautomers namely pentane-2,4-dione and 4-hydroxy-pent-3-en-2-one. The specific example of the imine-enamine isomerization is

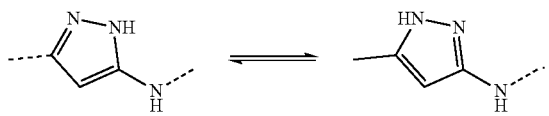

Unless otherwise stated, the term "enriching an isomer", "isomer enrichment", "enriching an enantiomer" or "enantiomer enrichment" means that the content of one isomer or enantiomer is less than 100%, and the content of the isomer or enantiomer is more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise stated, the term "isomeric excess" or "enantiomeric excess" refers to a difference between relative percentages of two isomers or two enantiomers. For example, if the content of one isomer or enantiomer is 90%, and the content of the other isomer or enantiomer is 10%, the value of isomeric or enantiomeric excess (ee value) is 80%.

The optically active (R)- and (S)-isomers and D and L isomers can be prepared by chiral synthesis or chiral reagents or other conventional techniques. If it is desired to obtain an enantiomer of a compound of the present disclosure, the enantiomer can be prepared by asymmetric synthesis or derivatization with chiral auxiliary agents, comprising separating the resulting diastereomeric mixture, and cleaving the auxiliary group to obtain the pure desired enantiomer. Alternatively, when the molecule contains an alkaline functional group (such as amino) or an acidic functional group (such as carboxyl), it together with an appropriate optically active acid or alkali forms a diastereomeric salt, the diastereoisomers are resolved through a conventional method known in the art, and the pure enantiomers are recovered and obtained. In addition, the separation of enantiomers and diastereomers is usually accomplished by using chromatography with a chiral stationary phase, and optionally combined with a chemical derivatization method (for example, carbamate is formed from amine).

The compound of the present disclosure can contain non-natural proportions of atomic isotopes on one or more atoms constituting this compound. For example, compounds can be labeled with radioisotopes, such as tritium ($^3H$), iodine-125 ($^{121}I$), or C-14 ($^4C$). Again, for example, hydrogen can be substituted by heavy hydrogen to form a deuterated drug. The bond consisting of deuterium and carbon is firmer than the bond formed by ordinary hydrogen and carbon. Compared with an undeuterated drug, the deuterated drug has the advantages of reduced toxic and side effects, increased drug stability, enhanced curative efficacy and prolonged biological half-life. Transformations in all the isotopes of the compound of the present disclosure, whether radioactive or not, are included in the scope of the present disclosure.

"Optional" or "optionally" means that the subsequently described events or conditions possibly but unnecessarily occur, and this description includes a situation in which the event or condition occurs and a situation in which the event or condition does not occur.

The term "substituted" means that any one or more hydrogen atoms on a particular atom are substituted by substituents, and deuterium and hydrogen variants can be included, as long as the valence of the particular atom is normal and the substituted compound is stable. When the substituent is oxygen (namely, =O), it means that two hydrogen atoms are substituted. Oxygen substitution does not occur on aromatic groups. The term "optionally substituted" means that it can be substituted or not substituted. Unless otherwise specified, the type and number of substituents may vary randomly as long as they are chemically achievable.

When any variable (for example R) occurs more than once in the composition or structure of a compound, its definition is independent in each case. Thus, for example, if one group is substituted with 0-2 R, the group may be optionally substituted with at most two R, and the substituent R is independently selected in each case. In addition, combinations of substituents and/or variants thereof are allowable only if such combinations can generate stable compounds.

When the number of a linking group is 0, such as —(CRR)$_0$—, it means that this linking group is a single bond.

When one of the variables is selected from a single bond, it means that the two groups linked thereby are directly linked. For example, when L in A-L-Z represents the single bond, this structure is actually A-Z.

When one substituent is absent, it means that the substituent does not exist. For example, when X in A-X is absent, it means that the structure is actually A.

When the linking group listed does not indicate its linking direction, the linking direction is arbitrary, for example, when the linking group L in

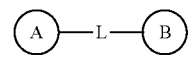

is -M-W—, -M-W— can link ring A and ring B in the direction same as the reading sequence from left to right to form

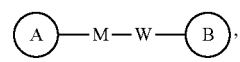

or link ring A and ring B in the direction opposite to the reading sequence from left to right to form

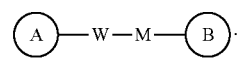

The combination of the linking groups, substituents and/or variants thereof can be allowable only if such the combination can generate a stable compound.

Unless otherwise specified, the term "C1-6 alkyl" is used to represent a linear or branched saturated hydrocarbon group composed of 1-6 carbon atoms. The C1-6 alkyl includes C1-5 alkyl, C1-4 alkyl, C1-3 alkyl, C1-2 alkyl, C2-6 alkyl, C2-4 alkyl, C6 alkyl and C5 alkyl. The C1-6 alkyl may be monovalent (such as methyl), divalent (such as methylene) or multivalent (such as methine). Examples of C1-6 alkyl include but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl, and the like.

Unless otherwise specified, the term "$C_{1-3}$ alkyl" is used to represent a linear or branched saturated hydrocarbon group composed of 1-3 carbon atoms. The $C_{1-3}$ alkyl includes $C_{1-2}$ alkyl and $C_{2-3}$ alkyl. The $C_{1-3}$ alkyl may be monovalent (such as methyl), divalent (such as methylene) or multivalent (such as methine). Examples of $C_{1-3}$ alkyl include but are not limited to methyl (Me), ethyl (Et) and propyl (including n-propyl and isopropyl), and the like.

Unless otherwise specified, $C_{n-n+m}$ or $C_n$—$C_{n+m}$ includes any specific condition of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$. Similarly, n member to n+m member means that the number of atoms in the ring is from n to n+m, for example, 3-12 membered ring includes 3-membered ring, 4-membered ring, 5-membered ring, 6-membered ring, 7-membered ring, 8-membered ring, 9-membered ring, 10 membered ring, 11-membered ring and 12-membered ring, and also includes any range from n to n+m, for example, 3-12 membered ring includes 3-6 membered ring, 3-9 membered ring, 5-6 membered ring, 5-7 membered ring, 6-7 membered ring, 6-8 membered ring and 6-10 membered ring.

Unless otherwise specified, the term "halo" or "halogen" alone or as a part of another substituent represents a fluorine, chlorine, bromine or iodine atom.

The term "leaving group" refers to a functional group or an atom that can be substituted by another functional group or atom through substitution reaction (for example, affinity substitution reaction). For example, representative leaving groups include trifluoromethanesulfonate; chlorine, bromine, and iodine; sulfonate groups such as mesylate, tosylate, p-bromobenzenesulfonate, p-toluenesulfonate; acyloxy groups, such as acetoxy and trifluoroacetoxy.

The term "protecting group" includes but is not limited to "amino protecting group", "hydroxyl protecting group" or "thiol protecting group". The term "amino protecting group" refers to a protecting group suitable for preventing side reaction at a nitrogen position of amino. Representative amino protecting groups include but are not limited to formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl) methyl; silyl, such as trimethylsilyl (TMS) and tert-butyldimethylsilyl (TBS), and the like. The term "hydroxyl protecting group" refers to a protecting group suitable for preventing side reaction of hydroxyl. Representative hydroxyl protecting groups include but are not limited to alkyl, such as methyl, ethyl and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyl dimethylsilyl (TBS), and the like.

The compound of the present disclosure can be prepared by various synthetic methods well known to those skilled in the art, including specific embodiments listed below, embodiments formed by combining the specific embodiments listed below with other chemical synthesis methods, and equivalent replacement manners well known to those skilled in the art. The preferred embodiments include but are not limited to the embodiments of the present disclosure.

The solvents used in the present disclosure are commercially available. The following abbreviations are used in the present disclosure: eq means equivalent amount or equal amount; M means mol/L; DMSO means dimethyl sulfoxide; EtOH means ethanol; Boc means tert-butoxycarbonyl; TFA means trifluoroacetic acid; p.o. means oral administration; BID meansadministration twice a day.

Compounds are named according to conventional naming principles in the art or using ChemDraw® software, and commercially available compounds are named based on the supplier's catalog name.

Technical Effect

The compound of the present disclosure exhibits good inhibitory activity against wild-type and V804M mutant RET. The compound of the present disclosure has an excellent pharmacokinetic property.

DETAILED DESCRIPTION

The present disclosure will be described in detail through examples below, but it is not intended to adversely limit the present disclosure. The present disclosure has been described in detail herein, in which the specific embodiments thereof have also been disclosed. For those skilled in the art, it will be obvious to make various variations and improvements to the specific embodiments of the present disclosure without departing from the spirits and scope of the present disclosure.

001 or 002

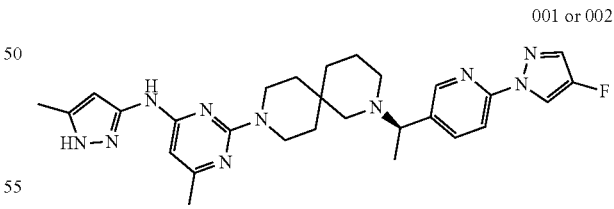

002 or 001

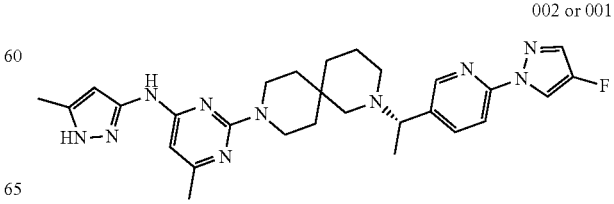

Synthetic Route:

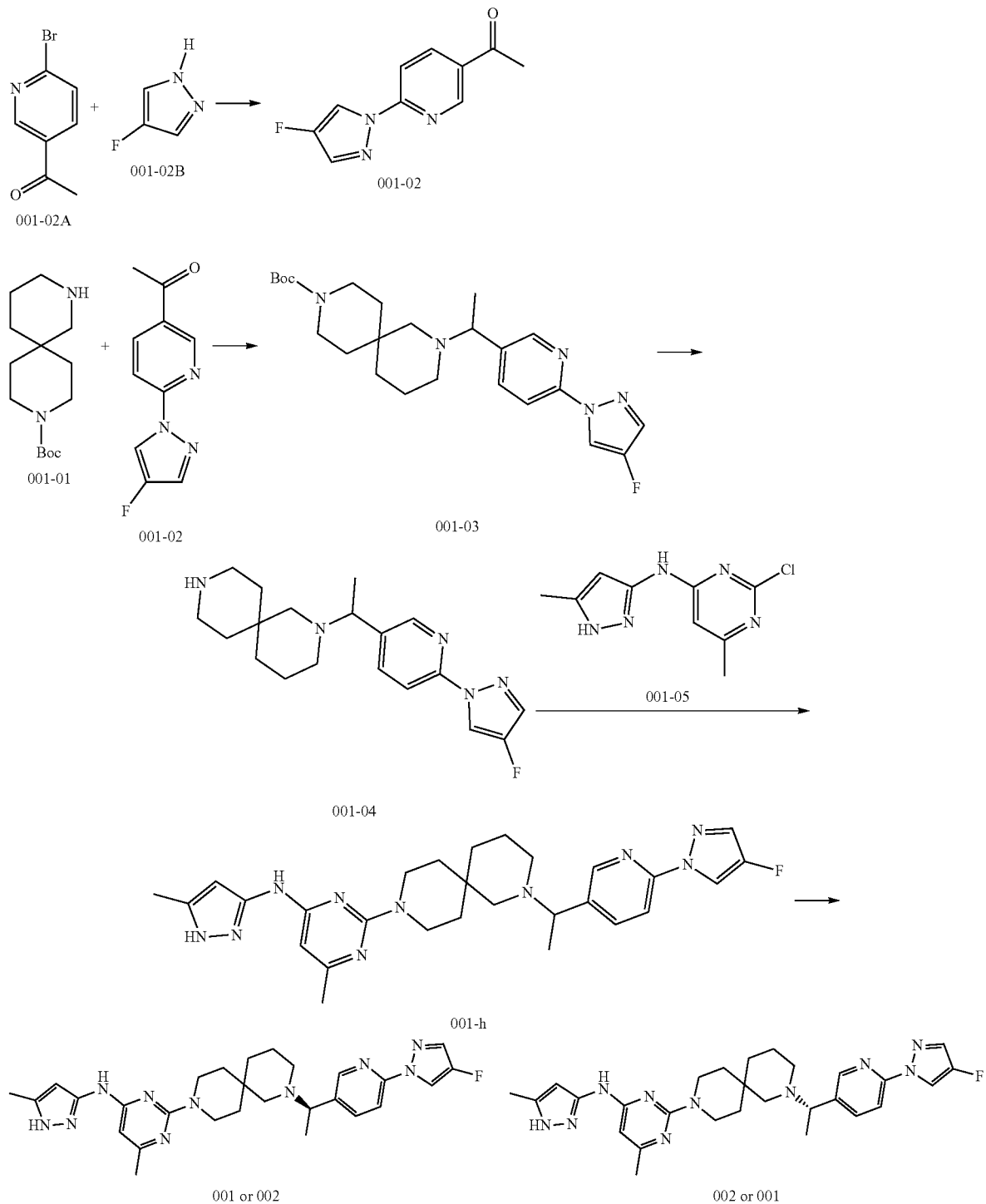

Step 1: Synthesis of Compound 001-02

001-02B (473.30 mg, 5.50 mmol, 1.1 eq), 001-02A (1.0 g, 5.00 mmol, 4.99 mL, 1.0 eq), potassium carbonate (1.73 g, 12.50 mmol, 2.5 eq) and N, N-dimethylformamide (2 mL) were added into a flask and stirred at 90° C. for 16 h. The reaction solution was diluted with 5 mL of dichloromethane and filtered, the solid was soaked in 5 mL of dichloromethane, and the obtained solution was stirred at 50° C. for 15 min and filtered hot, and two filtrates were combined and concentrated, diluted with 20 mL of ethyl acetate, and washed with 20 mL of saturated sodium sulfate for three times. The organic phase was dried with anhydrous sodium sulfate for 30 min, and dried by a spinning method to obtain compound 001-02.

Step 2: Synthesis of Compound 001-3

001-01 (150 mg, 731.04 μmol, 1 eq), 001-02 (278.93 mg, 1.10 mmol, 1.5 eq), titanium tetraisopropoxide (2 mL), sodium cyanoborohydride (229.70 mg, 3.66 mmol, 5.0 eq) and ethylene glycol dimethyl ether (10 mL) were added into a 10 mL flask, and stirred at 70° C. for 10 h. 20 mL of water was added, insoluble substances were removed by filtration, the filtrate was separated to obtain an organic phase, the organic phase was dried by a spinning method to obtain a crude product, and the crude product was purified by column chromatography (ethyl acetate:petroleum ether=0-33%) to obtain compound 001-03. LCMS: MS (ESI) m/z: 444.2 $[M+1]^+$.

Step 3: Synthesis of Compound 001-04

001-03 (160 mg, 338.18 μmol, 1 eq) was added into a 50 mL flask, hydrogen chloride/dioxane (1 mL) was added, and the reaction solution was stirred at 25° C. for 6 h. The reaction solution was dried by a spinning method to obtain a crude product 001-04. LCMS: MS (ESI) m/z: 344.1 $[M+1]^+$.

Step 4: Synthesis of Compound 001 and Compound 002

001-05 (50 mg, 223.55 μmol, 1.0 eq), 001-04 (115.17 mg, 335.33 μmol, 1.5 eq), diisopropylethylamine (130.01 mg, 1.01 mmol, 175.22 μL, 4.5 eq) and isopropanol (2 mL) were added into a 50 mL flask, and subjected to microwave reaction for 1 h at 120° C. The reaction solution was dried by a spinning method to obtain a crude product. The crude product was initially purified by column chromatography (methanol:dichloromethane=0-5%) to obtain 001-h, and 001-h was separated by a chiral preparative column (chromatographic column: DAICEL CHIRALPAK AS (250 mm×30 mm, 10 μm); mobile phase: [A: $CO_2$ B: 0.1% ammonia water ethanol]; B %: 50%-50%) to obtain target compounds namely compound 001 and compound 002.

Compound 001 (peak position: 0.949 min)

$^1$H NMR (400 MHz, deuterated methanol) δ ppm 1.16-1.46 (m, 5H) 1.55 (br s, 3H) 1.67 (br s, 3H) 2.19 (s, 3H) 2.31 (s, 2H) 2.36 (brs, 2H) 2.64 (br s, 1H) 3.44-3.68 (m, 3H) 3.71-3.86 (m, 2H) 4.64 (s, 2H) 6.06 (br s, 1H) 6.22 (br s, 1H) 7.68 (d, J=4.27 Hz, 1H) 7.89-7.98 (m, 2H) 8.40 (s, 1H) 8.50 (d, J=4.27 Hz, 1H)

LCMS: MS (ESI) m/z: 531.1 $[M+1]^+$.

Compound 002 (peak position: 2.405 min)

$^1$H NMR (400 MHz, deuterated methanol) δ ppm 1.16-1.46 (m, 5H) 1.55 (br s, 3H) 1.67 (br s, 3H) 2.19 (s, 3H) 2.31 (s, 2H) 2.36 (br s, 2H) 2.64 (br s, 1H) 3.44-3.68 (m, 31H) 3.71-3.86 (m, 2H) 4.64 (s, 2H) 6.06 (br s, 1H) 6.22 (br s, 1H) 7.68 (d, J=4.27 Hz, 1H) 7.89-7.98 (m, 2H) 8.40 (s, 1H) 8.50 (d, J=4.27 Hz, 1H) LCMS: MS (ESI) m/z: 531.1 $[M+1]^+$.

Example 2

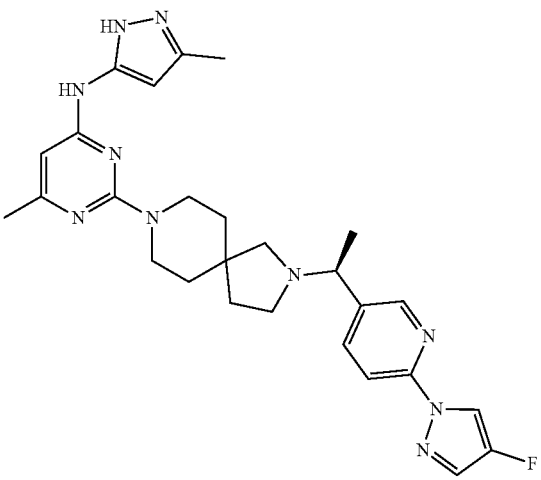

003 or 004

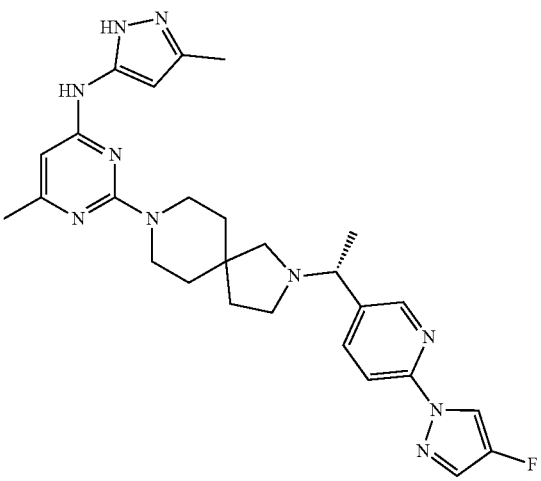

004 or 003

Synthetic Route:

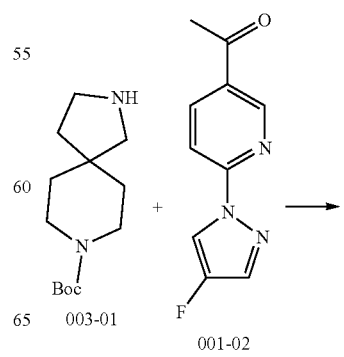

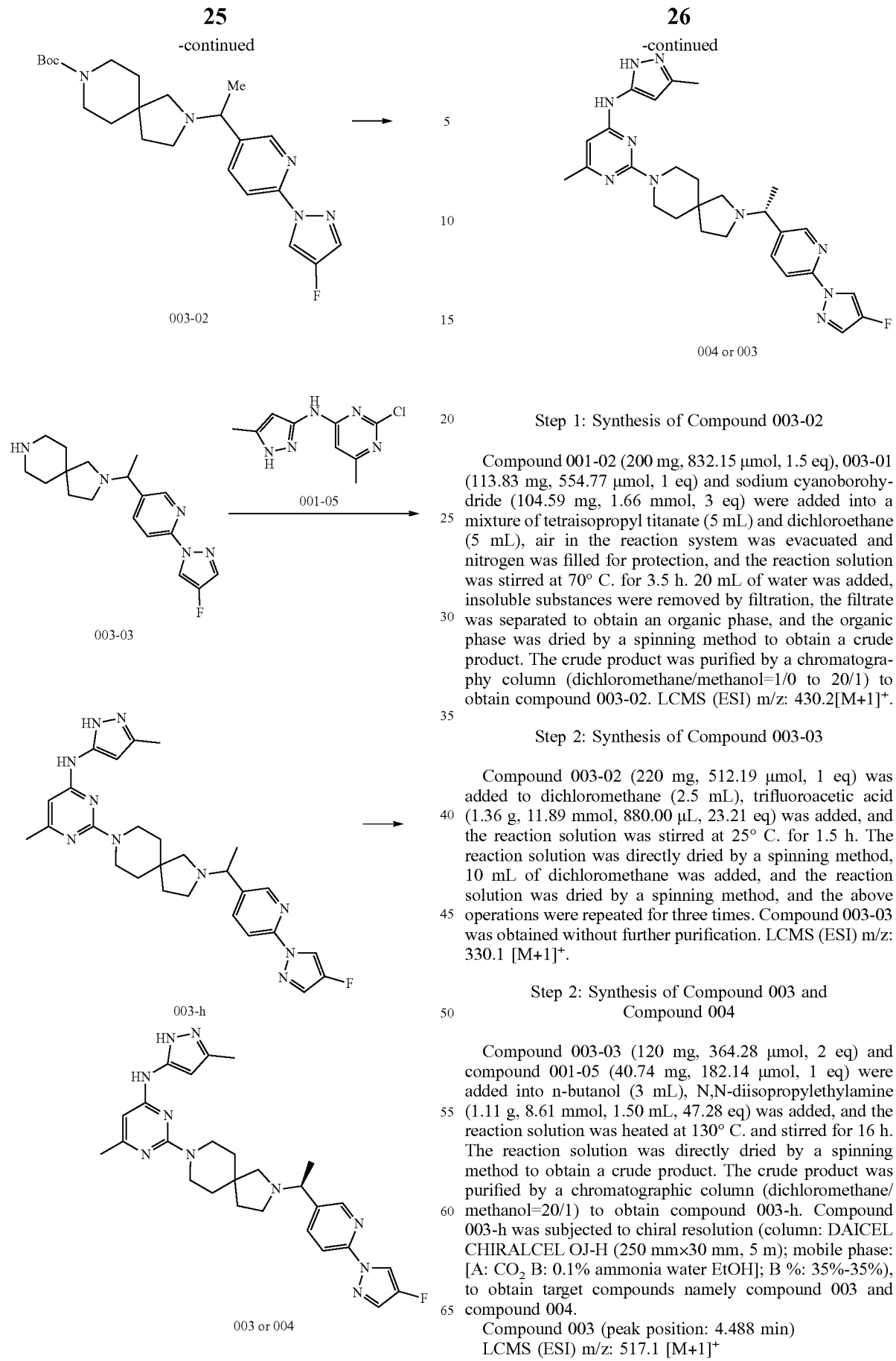

Step 1: Synthesis of Compound 003-02

Compound 001-02 (200 mg, 832.15 μmol, 1.5 eq), 003-01 (113.83 mg, 554.77 μmol, 1 eq) and sodium cyanoborohydride (104.59 mg, 1.66 mmol, 3 eq) were added into a mixture of tetraisopropyl titanate (5 mL) and dichloroethane (5 mL), air in the reaction system was evacuated and nitrogen was filled for protection, and the reaction solution was stirred at 70° C. for 3.5 h. 20 mL of water was added, insoluble substances were removed by filtration, the filtrate was separated to obtain an organic phase, and the organic phase was dried by a spinning method to obtain a crude product. The crude product was purified by a chromatography column (dichloromethane/methanol=1/0 to 20/1) to obtain compound 003-02. LCMS (ESI) m/z: 430.2[M+1]$^+$.

Step 2: Synthesis of Compound 003-03

Compound 003-02 (220 mg, 512.19 μmol, 1 eq) was added to dichloromethane (2.5 mL), trifluoroacetic acid (1.36 g, 11.89 mmol, 880.00 μL, 23.21 eq) was added, and the reaction solution was stirred at 25° C. for 1.5 h. The reaction solution was directly dried by a spinning method, 10 mL of dichloromethane was added, and the reaction solution was dried by a spinning method, and the above operations were repeated for three times. Compound 003-03 was obtained without further purification. LCMS (ESI) m/z: 330.1 [M+1]$^+$.

Step 2: Synthesis of Compound 003 and Compound 004

Compound 003-03 (120 mg, 364.28 μmol, 2 eq) and compound 001-05 (40.74 mg, 182.14 μmol, 1 eq) were added into n-butanol (3 mL), N,N-diisopropylethylamine (1.11 g, 8.61 mmol, 1.50 mL, 47.28 eq) was added, and the reaction solution was heated at 130° C. and stirred for 16 h. The reaction solution was directly dried by a spinning method to obtain a crude product. The crude product was purified by a chromatographic column (dichloromethane/methanol=20/1) to obtain compound 003-h. Compound 003-h was subjected to chiral resolution (column: DAICEL CHIRALCEL OJ-H (250 mm×30 mm, 5 m); mobile phase: [A: CO$_2$ B: 0.1% ammonia water EtOH]; B %: 35%-35%), to obtain target compounds namely compound 003 and compound 004.

Compound 003 (peak position: 4.488 min)
LCMS (ESI) m/z: 517.1 [M+1]$^+$

¹H NMR (400 MHz, deuterated methanol) δ ppm 1.45 (d, J=6.53 Hz, 3H) 1.60 (q, J=6.02 Hz, 4H) 1.70-1.82 (m, 2H) 2.19 (s, 3H) 2.28 (s, 3H) 2.40 (d, J=9.29 Hz, 1H) 2.47-2.62 (m, 2H) 2.72-2.83 (m, 1H) 3.57-3.71 (m, 2H) 3.73-3.93 (m, 2H) 6.04 (s, 1H) 5.92-6.08 (m, 1H) 6.15 (s, 1H) 7.69 (d, J=4.02 Hz, 1H) 7.86-8.02 (m, 2H) 8.39 (d, J=1.25 Hz, 1H) 8.51 (d, J=4.27 Hz, 1H)
Compound 004 (peak position: 4.755 min)
LCMS (ESI) m/z: 517.1 [M+1]⁺
¹H NMR (400 MHz, deuterated methanol) δ ppm 1.45 (d, J=6.53 Hz, 3H) 1.60 (q, J=6.19 Hz, 4H) 1.69-1.81 (m, 2H) 2.19 (s, 3H) 2.28 (s, 3H) 2.39 (d, J=9.79 Hz, 1H) 2.45-2.60 (m, 2H) 2.73-2.83 (m, 1H) 3.60-3.70 (m, 2H) 3.73-3.93 (m, 2H) 6.04 (s, 1H) 5.92-6.08 (m, 1H) 6.14 (s, 1H) 7.67-7.72 (m, 1H) 7.89-8.00 (m, 2H) 8.39 (d, J=1.51 Hz, 1H) 8.51 (dd, J=4.52, 0.75 Hz, 1H)
Example 3
Synthetic Route:
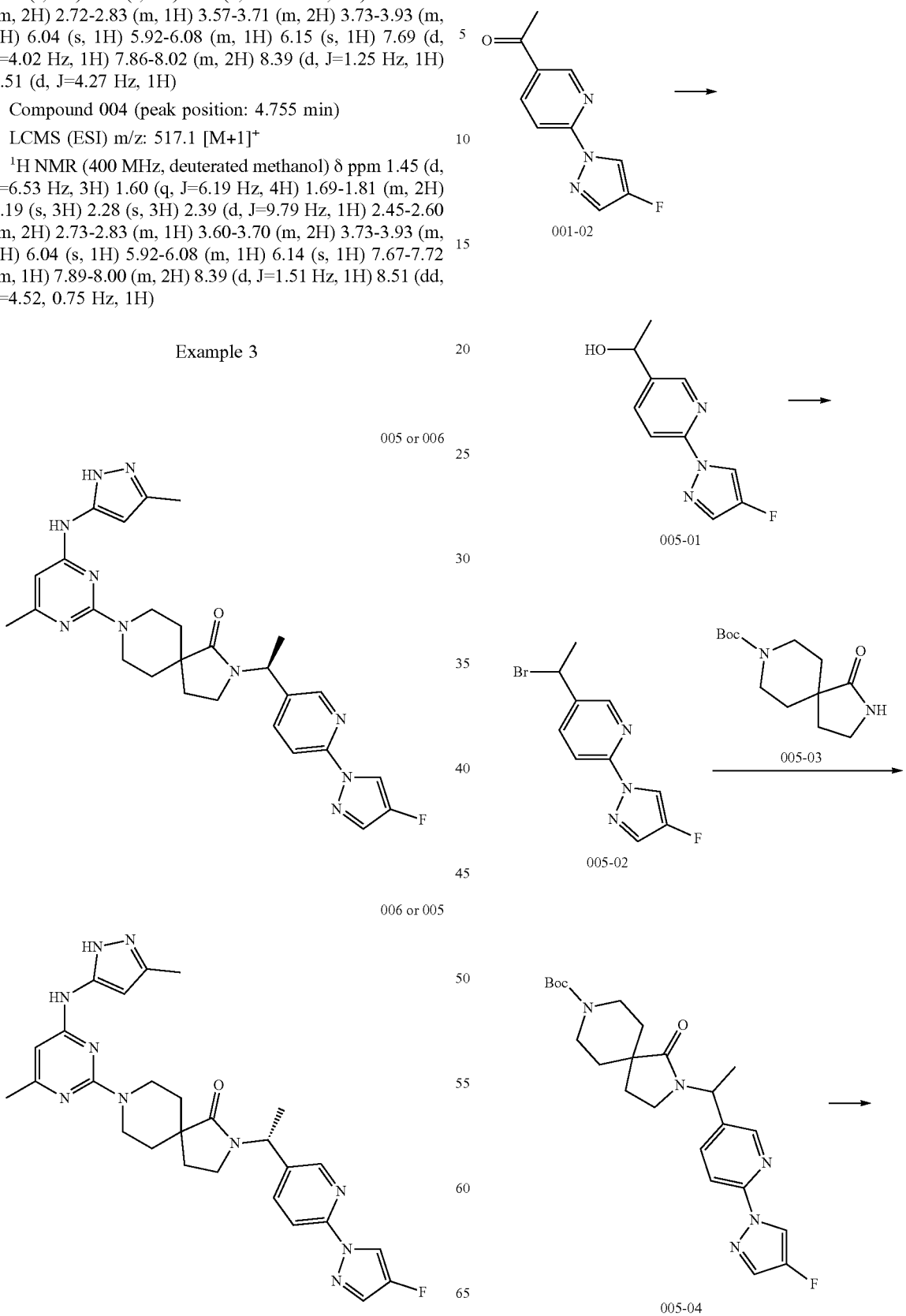

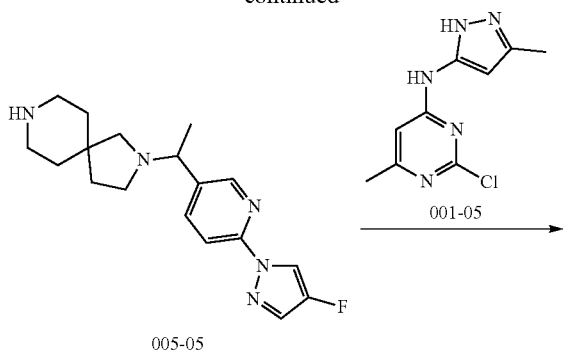

Step 1: Synthesis of Compound 005-01

Compound 001-02 was dissolved into a mixture of dichloromethane (5 mL) and methanol (10 mL), sodium borohydride (276.57 mg, 7.31 mmol, 3 eq) was added at 20° C., and the reaction solution was reacted for 0.5 h. The reaction solution was concentrated under reduced pressure at 43° C. The concentrate was dissolved into 30 mL of water and 30 mL of dichloromethane, and extracted, and meanwhile a water phase was extracted with dichloromethane (30 mL×3). Organic phases were combined and dried by a spinning method to obtain a crude product. The crude product was purified by a chromatographic column (petroleum ether/ethyl acetate=3:1) to obtain compound 005-01, for using in the next step.

Step 2: Synthesis of Compound 005-02

Compound 005-01 was dissolved into dichloromethane (5 mL), dibromosulfoxide (5.02 g, 24.13 mmol, 1.87 mL, 10 eq) was added dropwise at 0° C., and the mixture was stirred at 50° C. for 3 h. The reaction solution was concentrated under reduced pressure at 43° C. The concentrate was dissolved into 10 mL of dichloromethane, and concentrated under reduced pressure. The above operations were repeated for three times. The resulting crude product was purified by a chromatographic column (petroleum ether/ethyl acetate=5/1) to obtain compound 005-02. LCMS (ESI) m/z: 269.8 [M+1]$^+$.

Step 3: Synthesis of Compound 005-04

Compound 005-03 (155.36 mg, 610.88 μmol, 1.1 eq), sodium hydride (26.65 mg, 666.42 μmol, 60% purity, 1.2 eq) were added into N,N-dimethylformamide (3 mL) at 0° C., air in the reaction system was evacuated and nitrogen was filled for protection, compound 005-02 (150 mg, 555.35 μmol, 1 eq) was added after stirring the reaction solution for 10 min, and the reaction solution was stirred for 2.5 h at 20° C. Water was added into 10 mL of the reaction solution, and a water phase was extracted for three times with 10 mL of ethyl acetate. The organic phase was collected, dried with anhydrous sodium sulfate, and dried by a spinning method to obtain a crude product. The crude product was purified by a chromatographic column (petroleum ether/ethyl acetate=3/1) to obtain compound 005-04. LCMS (ESI) m/z: 344.3 [M-Boc+1]$^+$.

Step 4: Synthesis of Compound 005-05

Compound 005-04 (100 mg, 225.47 μmol, 1 eq) was added into dichloromethane (5 mL), trifluoroacetic acid (2.57 g, 22.51 mmol, 1.67 mL, 99.84 eq) was added, and reaction solution was stirred at 25° C. for 1.5 h. The reaction solution was directly dried by a spinning method, 10 mL of dichloromethane was added for drying by a spinning method, and the above operations were repeated for 3 times. Compound 005-05 was obtained without further purification. LCMS (ESI) m/z: 344.4 [M+1]$^+$.

Step 5: Synthesis of Compounds 005 and 006

Compound 005-05 (50 mg, 145.60 μmol, 1 eq) and compound 001-05 (32.57 mg, 145.60 μmol, 1 eq) were added into n-butanol (3 mL), N,N-diisopropylethylamine (742.00 mg, 5.74 mmol, 1 mL, 39.43 eq) was added, and the reaction solution was heated and stirred at 130° C. for 16 h. The reaction solution was directly dried by a spinning method to obtain a crude product. The crude product is purified by a high performance liquid chromatographic column (column: Waters Xbridge BEH C18 150×25 mm, 5 μm; mobile phase: [water (10 mM ammonium bicarbonate)-acetonitrile]; acetonitrile %: 37%-67%, 9.5 min) to obtain compound 005-h. Compound 005-h was separated by a chiral preparative column: (DAICEL CHIRALPAK AS-H (250 mm×30 mm, 5 μm); mobile phase: [A: $CO_2$, B: 0.1% ammonia water-ethanol]; B %: 50%-50%) to obtain target compounds namely compound 005 and compound 006.
005-h $^1$H NMR (400 MHz, deuterated methanol) δ ppm 1.42 (d, J=13.80 Hz, 1H) 1.48-1.57 (m, 1H) 1.62 (d, J=7.28 Hz, 3H) 1.85 (qd, J=12.51, 4.39 Hz, 2H) 2.01-2.16 (m, 2H) 2.20 (s, 3H) 2.26 (s, 3H) 3.04-3.21 (m, 3H) 3.43-3.60 (m, 1H) 4.51-4.69 (m, 2H) 5.42 (q, J=6.94 Hz, 1H) 5.87-6.45 (m, 2H) 7.69 (d, J=4.02 Hz, 1H) 7.86-7.91 (m, 1H) 7.91-7.97 (m, 1H) 8.37 (d, J=1.76 Hz, 1H) 8.51 (d, J=4.27 Hz, 1H)

Target compound 005 (peak position: 4.323)
LCMS (ESI) m/z: 531.5 [M+1]$^+$ $^1$H NMR (400 MHz, deuterated methanol) δ ppm 1.42 (d, J=13.80 Hz, 1H) 1.48-1.57 (m, 1H) 1.62 (d, J=7.28 Hz, 3H) 1.85 (qd, J=12.51, 4.39 Hz, 2H) 2.01-2.16 (m, 2H) 2.20 (s, 3H) 2.26 (s, 3H) 3.04-3.21 (m, 3H) 3.43-3.60 (m, 1H) 4.51-4.69 (m, 2H) 5.42 (q, J=6.94 Hz, 1H) 5.87-6.45 (m, 2H) 7.69 (d, J=4.02 Hz, 1H) 7.86-7.91 (m, 1H) 7.91-7.97 (m, 1H) 8.37 (d, J=1.76 Hz, 1H) 8.51 (d, J=4.27 Hz, 1H)

Target compound 006 (peak position: 5.496)
LCMS (ESI) m/z: 531.5 [M+1]$^+$ $^1$H NMR (400 MHz, deuterated methanol) δ ppm 1.42 (d, J=13.80 Hz, 1H) 1.48-1.57 (m, 1H) 1.62 (d, J=7.28 Hz, 3H) 1.85 (qd, J=12.51, 4.39 Hz, 2H) 2.01-2.16 (m, 2H) 2.20 (s, 3H) 2.26 (s, 3H) 3.04-3.21 (m, 3H) 3.43-3.60 (m, 1H) 4.51-4.69 (m, 2H) 5.42 (q, J=6.94 Hz, 1H) 5.87-6.45 (m, 2H) 7.69 (d, J=4.02 Hz, 1H) 7.86-7.91 (m, 1H) 7.91-7.97 (m, 1H) 8.37 (d, J=1.76 Hz, 1H) 8.51 (d, J=4.27 Hz, 1H)

Example 4

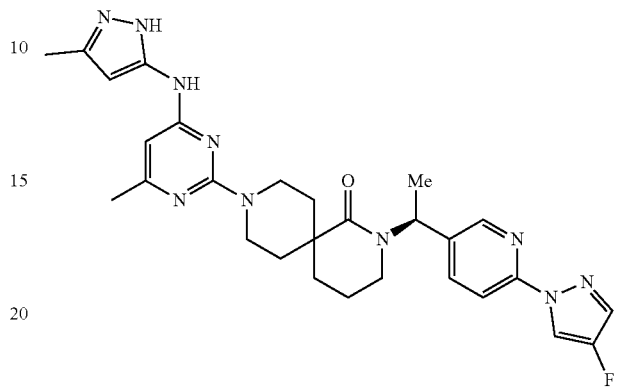

007 or 008

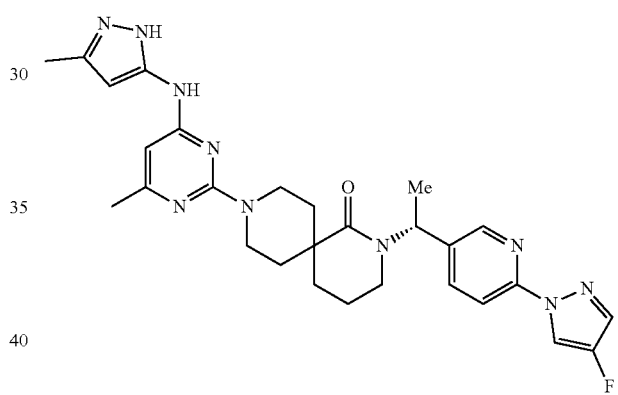

008 or 007

Synthetic Route:

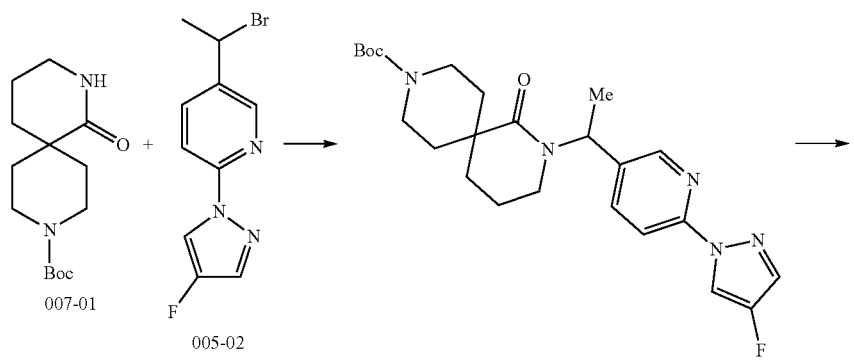

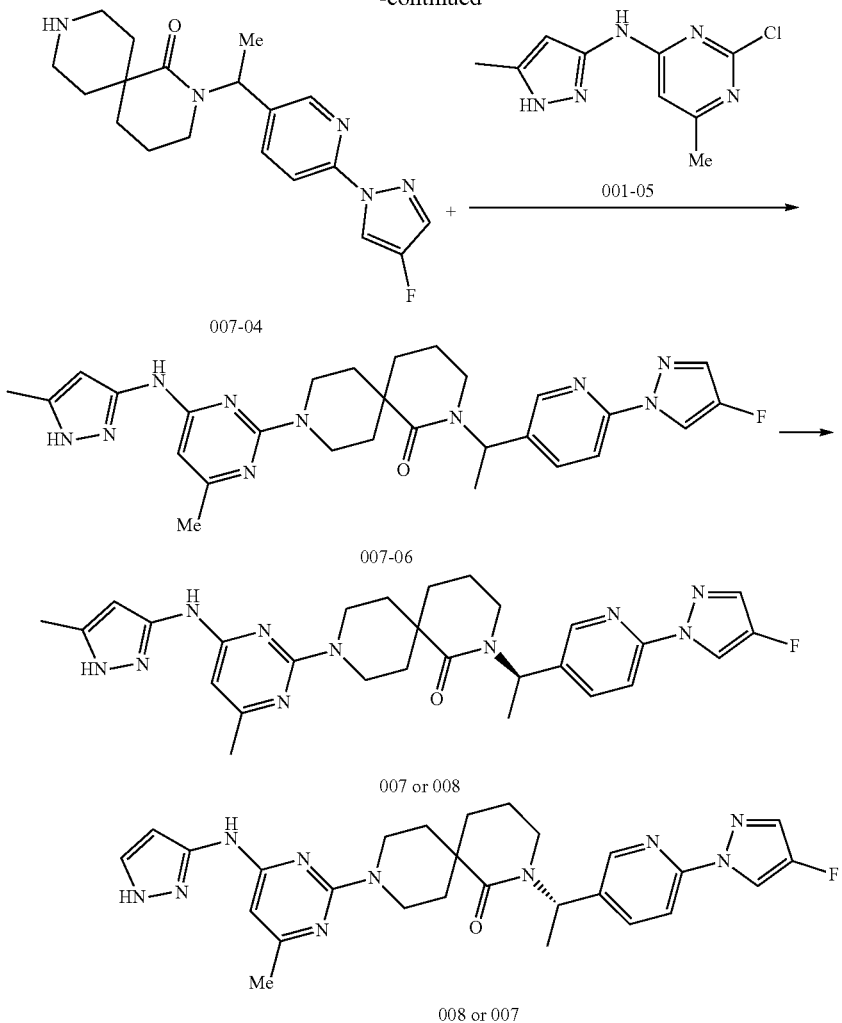

Step 1: Synthesis of Compound 007-03

007-01 (323.96 mg, 2.50 mmol, 1.2 eq) and N,N-dimethylformamide (0.2 mL) were added into a 10 mL flask, nitrogen was pumped and replaced for three times, sodium hydride (125.03 mg, 3.13 mmol, 60% purity, 1.5 eq) was added at 0° C., the reaction solution was stirred at 25° C. for 30 min, and 005-02 (500 mg, 2.08 mmol, 1 eq) was added and stirred for 6 h. The reaction solution was washed with 10 mL of water and extracted with ethyl acetate (10 mL×3). The organic phases were combined, dried with anhydrous sodium sulfate, and dried by a spinning method to obtain a crude product. The crude product was purified by column chromatography to obtain compound 007-03. LCMS: MS (ESI) m/z: 358.4 [M-Boc+1]⁺.

Step 2: Synthesis of Compound 007-04

007-03 (140 mg, 305.98 μmol, 1 eq), a hydrochloric acid/dioxane solution (4 M, 764.96 μL, 10 eq) and dioxane (0.5 mL) were added into a 10 mL flask, and stirred at 25° C. for 6 h. The reaction solution was dried by a spinning method to obtain a crude product 007-04.

LCMS: MS (ESI) m/z: 358.3 [M+1]⁺.

Step 3: Synthesis of Compound 007-06

001-05 (62.58 mg, 279.78 μmol, 1.0 eq), 007-04 (100 mg, 279.78 μmol, 1.0 eq), diisopropylethylamine (162.71 mg, 1.26 mmol, 219.29 L, 4.5 eq) and isopropanol (2 mL) were added into a 50 mL flask, and stirred at 120° C. for 30 min under microwave. The reaction solution was dried by a spinning method, and purified by preparative chromatography (chromatographic column: Agela ASB 150×25 mm×5 μm; mobile phase: [water (0.05% HCl)-ACN]; acetonitrile %: 25%-45%, 10 min) to obtain 007-06. 007-06 was separated by a chiral preparative column (separation conditions: chromatographic column: DAICEL CHIRALPAK AS (250 mm×30 mm, 10 μm); mobile phase: [A: CO₂ B: 0.1% ammonia EtOH]; B %: 55%-55%) to obtain target compound 007 and compound 008.

Target compound 007 (peak position: 4.002 min) ¹H NMR (400 MHz, deuterated methanol) δ ppm 1.57 (br s, 1H) 1.60 (d, J=7.28 Hz, 3H) 1.65 (br s, 1H) 1.76-1.94 (m, 3H) 1.99-2.09 (m, 2H) 2.09-2.20 (m, 2H) 2.22 (s, 3H) 2.28 (s, 3H) 2.92-3.01 (m, 1H) 3.21-3.30 (m, 2H) 3.34-3.39 (m, 1H) 4.41-4.54 (m, 2H) 5.98 (q, J=7.28 Hz, 1H) 6.06-6.23 (m, 1H) 7.71 (d, J=4.27 Hz, 1H) 7.82-7.89 (m, 1H) 7.91-7.97 (m, 1H) 8.35 (d, J=2.26 Hz, 1H) 8.52 (d, J=4.52 Hz, 11H).

LCMS: MS (ESI) m/z: 545.0 [M+1]⁺.

Target compound 008 (peak position: 6.072 min)
¹H NMR (400 MHz, deuterated methanol) δ ppm 1.57 (br s, 1H) 1.60 (d, J=7.28 Hz, 3H) 1.65 (br s, 1H) 1.76-1.94 (m, 31H) 1.99-2.09 (m, 2H) 2.09-2.20 (m, 2H) 2.22 (s, 3H) 2.28 (s, 3H) 2.92-3.01 (m, 1H) 3.21-3.30 (m, 2H) 3.34-3.39 (m, 1H) 4.41-4.54 (m, 2H) 5.98 (q, J=7.28 Hz, 1H) 6.06-6.23 (m, 1H) 7.71 (d, J=4.27 Hz, 1H) 7.82-7.89 (m, 1H) 7.91-7.97 (m, 1H) 8.35 (d, J=2.26 Hz, 1H) 8.52 (d, J=4.52 Hz, 1H).
LCMS: MS (ESI) m/z: 545.4 [M+1]⁺.
Example 5
009 or 010 or 011 or 012
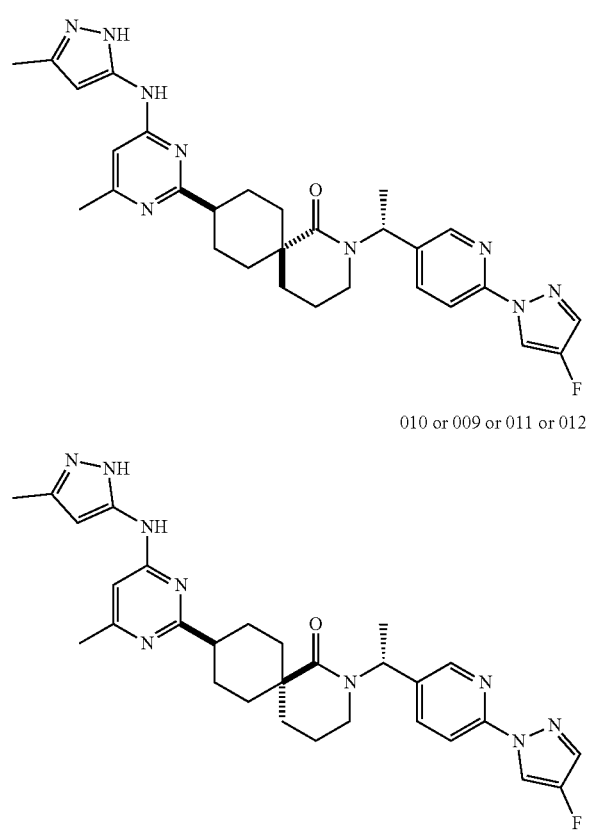
010 or 009 or 011 or 012
011 or 009 or 010 or 012
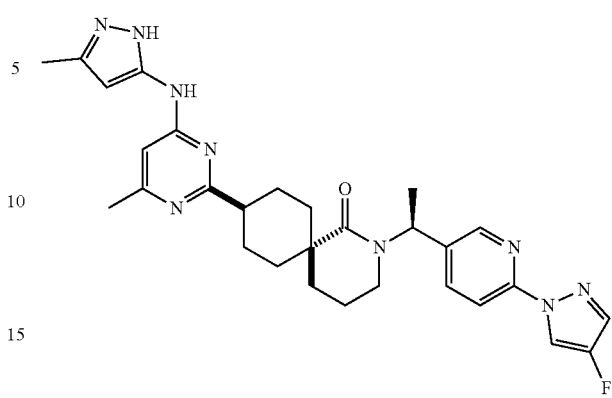
012 or 009 or 010 or 011
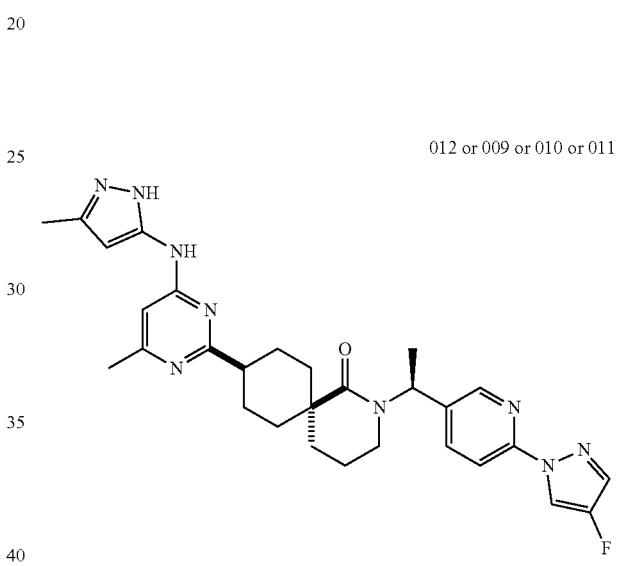
Synthetic Route:
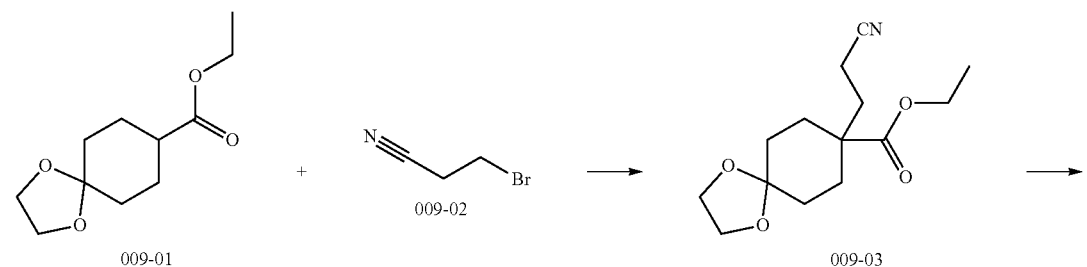

-continued
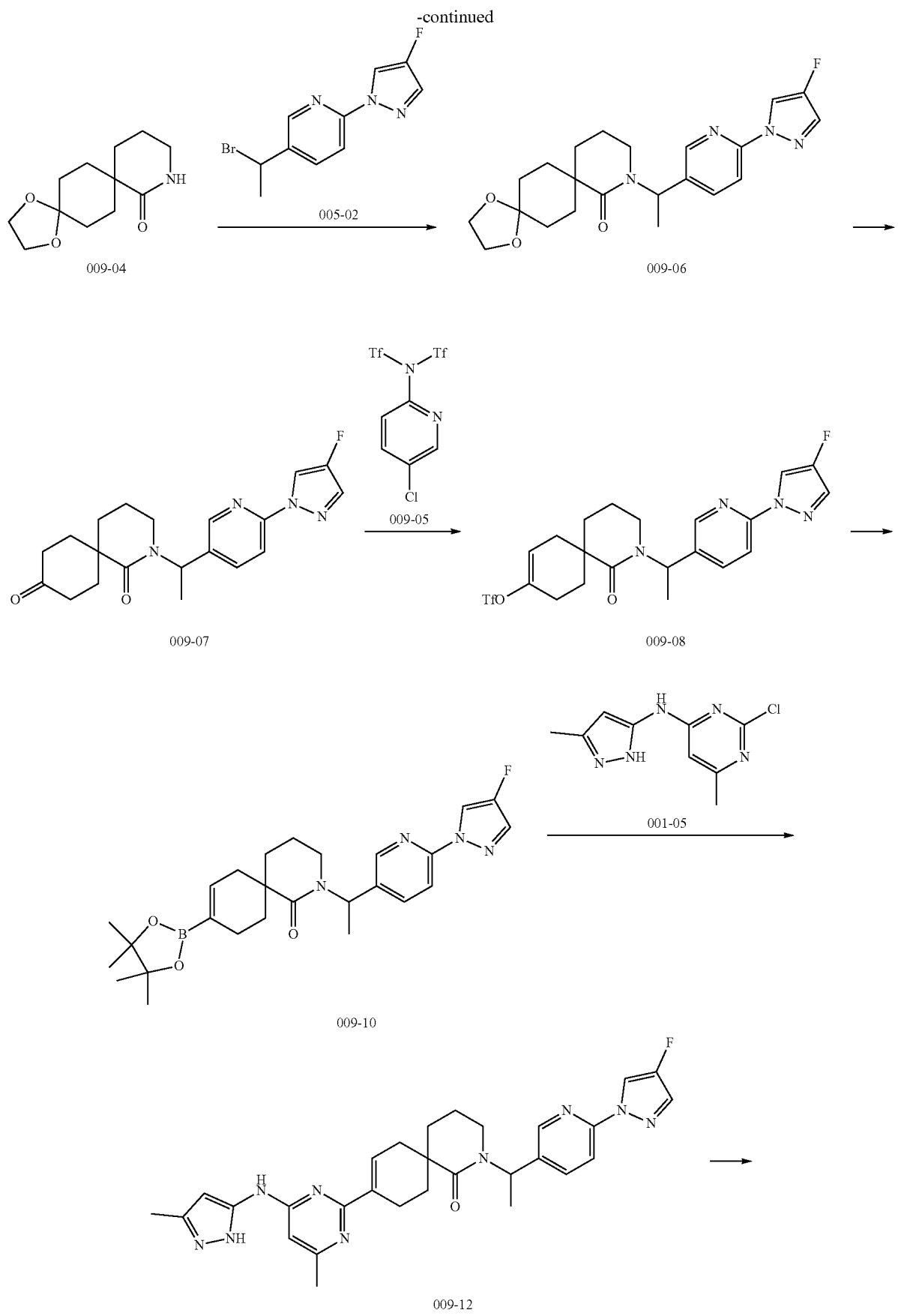

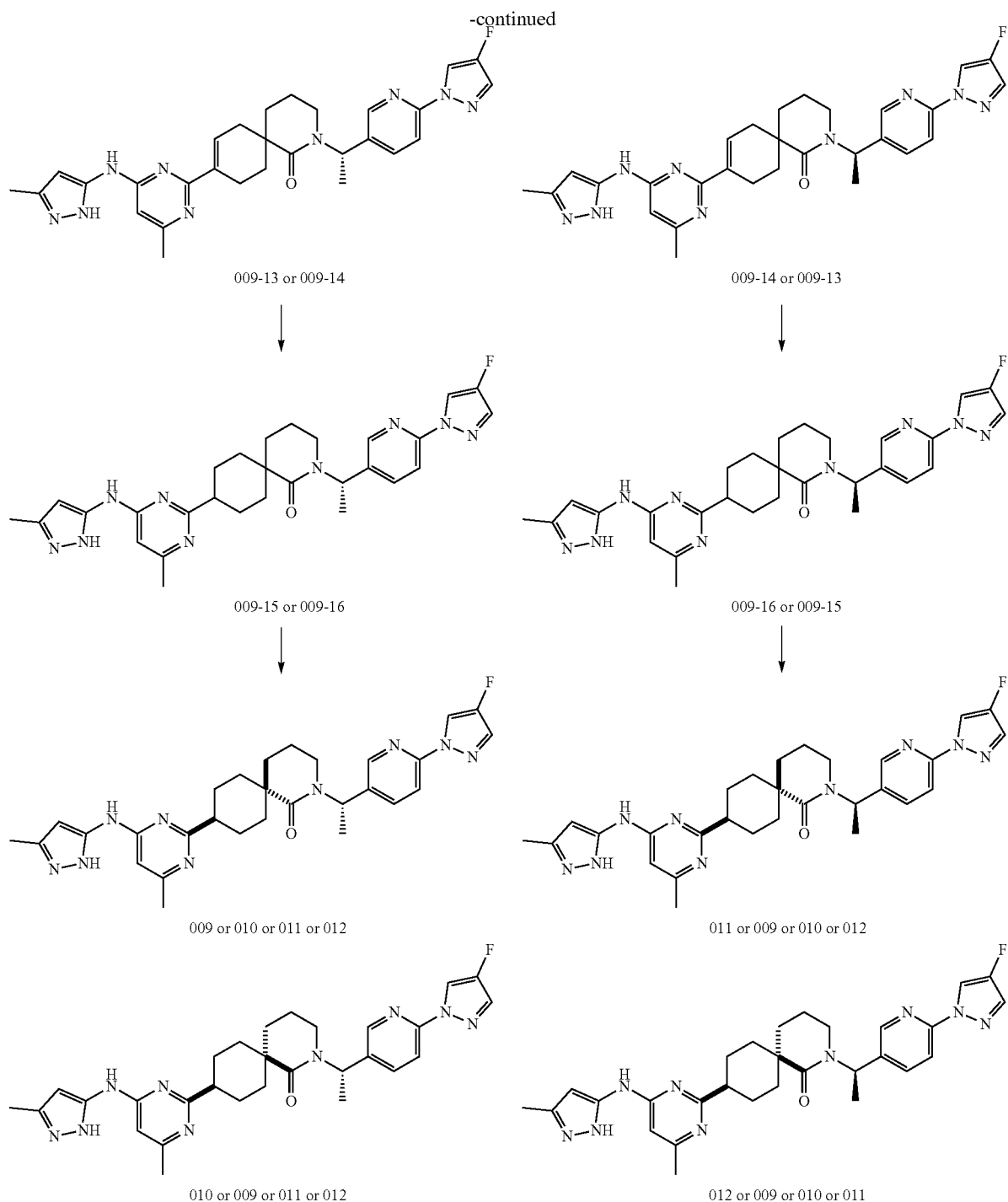

Step 1: Synthesis of Compound 009-03

009-1 (20 g, 93.35 mmol, 1 eq) was dissolved into tetrahydrofuran (100 mL) under nitrogen atmosphere at −78° C., lithium diisopropylamide (2 M, 51.34 mL, 1.1 eq) was slowly dropwise added, the reaction solution was stirred for 1 h at 0° C. and cooled to −78° C., bromopropionitrile (18.76 g, 140.02 mmol, 11.51 mL, 1.5 eq) was added, and the reaction solution was stirred at 25° C. for 16 h. 50 mL of a saturated ammonium chloride solution was added into the reaction solution. The reaction solution was extracted with 100 mL of ethyl acetate for three times, and organic phases were combined and dried by a spinning method to obtain a crude product. The crude product was purified by column chromatography to obtain 009-03. LCMS: MS (ESI) m/z: [M+1]$^+$ 268.2

Step 2: Synthesis of Compound 009-04

009-03 (12 g, 44.89 mmol, 1 eq), methanol (100 mL), raney nickel (384.57 mg, 4.49 mmol, 0.1 eq) and potassium carbonate (18.61 g, 134.67 mmol, 3.0 eq) were added into a IL hydrogenation flask, and reacted for 16 h at 45° C. under a hydrogen pressure of 45 psi. The reaction solution was filtered to remove insoluble substances. The filtrate was dried by a spinning method to obtain a crude product, and the crude product was purified by column chromatography to obtain 009-04. LCMS: MS (ESI) m/z: 226.1 [M+1]$^+$ Step 3: Synthesis of Compound 009-06

009-04 (2.2 g, 9.77 mmol, 1 eq), sodium hydride (468.70 mg, 11.72 mmol, 60% purity, 1.2 eq) and N,N-dimethylformamide (10 mL) were added at 0° C. and stirred for 30 min, and 005-02 (2.95 g, 10.94 mmol, 1.12 eq) was added. The reaction solution was stirred at 25° C. for 16 h. The reaction solution was spin-dried by an oil pump, 50 mL of water was added, and the reaction solution was extracted with 50 mL of ethyl acetate for three times, and organic phases were combined and dried by a spinning method to obtain a crude product. The crude product was purified by column chromatography to obtain 009-06. LCMS: MS (ESI) m/z: 415.1 [M+1]$^+$.

Step 4: Synthesis of Compound 009-07

009-06 (3.5 g, 8.44 mmol, 1 eq) was dissolved into tetrahydrofuran (20 mL), hydrochloric acid (12 M, 7.04 mL, 10 eq) was added, and the reaction solution was stirred at 45° C. for 4 h. 100 mL of a saturated sodium carbonate solution was added in the reaction solution under the pH of 9-10, and the reaction solution was extracted with 100 mL of dichloromethane for three times. The organic phases were combined and dried by a spinning method to obtain a crude product. The crude product was purified by column chromatography to obtain 009-07. LCMS: MS (ESI) m/z: 371.0 [M+1]$^+$.

Step 5: Synthesis of Compound 009-09

009-07 was added under nitrogen atmosphere at −78° C., tetrahydrofuran (40 mL) was added, lithium diisopropylamide (1 M, 5.67 mL, 1.4 eq) was slowly added dropwise, 009-08 was added after stirring the reaction solution for 30 min, and then the reaction solution was continued to stir for 16 h. 20 mL of saturated amine chloride was added into the reaction solution for quenching, and the reaction solution was extracted with 50 mL of dichloromethane for three times, and the organic phases were combined. The obtained crude product was purified by column chromatography to obtain 009-09. LCMS: MS (ESI) m/z: 503.1 [M+1]$^+$.

Step 6: Synthesis of Compound 009-10

009-09 (1.63 g, 3.24 mmol, 1 eq), bis(pinacolato)diboron (823.75 mg, 3.24 mmol, 1 eq), [1,1'-bis(diphenylphosphine)ferrocene]palladium dichloride dichloromethane complex (397.36 mg, 486.59 μmol, 0.15 eq), potassium acetate (318.36 mg, 3.24 mmol, 1 eq) and dioxane (20 mL) were added into a 100 mL flask, nitrogen was pumped for three times, and the reaction solution was reacted for 16 h at 110° C. The reaction solution was filtered to remove insoluble substances, the filtrate was dried by a spinning method to obtain a crude product. The crude product was purified by column chromatography to obtain 009-10. LCMS: MS (ESI) m/z: 480.9 [M+1]$^+$.

Step 7: Synthesis Compound 009-12

009-10 (500 mg, 1.04 mmol, 1 eq), 001-05 (246.76 mg, 1.10 mmol, 1.06 eq), [1,1'-bis(diphenylphosphine)ferrocene]palladium dichloride dichloromethane complex (85.00 mg, 104.00 μmol, 0.1 eq), potassium carbonate (431.20 mg, 3.12 mmol, 3.0 eq), dioxane (5 mL) and water (1.25 mL) were added into a 100 mL flask, nitrogen was pumped for three times, and the reaction solution was stirred for 2 h at 80° C. The reaction solution was filtered to remove insoluble substances, the filtrate was dried by a spinning method, 5 mL of methanol was added for dissolution, and the rustled solution was separated by preparative high performance liquid chromatography to obtain 009-12. Separation conditions were as below: column: Boston Green ODS 150×30 mm×5 μm; mobile phase: [water (0.075% trifluoroacetic acid)-acetonitrile]: acetonitrile %: 25%-55%, 12 min. LCMS: MS (ESI) m/z: 542.2 [M+1]$^+$.

Step 8: Synthesis of Compounds 009-13 and 14

009-12 (130 mg, 240.02 μmol, 1 eq) was separated by a chiral column to obtain 009-13 and 14. Separation conditions were as below: column: DAICEL CHIRALPAK AS-H (250 mm×30 mm, 5 μm); mobile phase: [A: CO$_2$, B: 0.1% ammonia water-methanol]; B %: 45%-45%.
013 LCMS: MS (ESI) m/z: 542.2 [M+1]$^+$
014 LCMS: MS (ESI) m/z: 542.2 [M+1]$^+$ Step 9: Synthesis of Compounds 009-15 and 009-16

009-13 (51 mg, 94.16 μmol, 1 eq), palladium on carbon (0.5 mg, 10% purity, 1.00 eq) and methanol (2 mL) were added into a 100 mL hydrogenation flask, and reacted for 16 h at 45° C. under the hydrogen pressure of 45 psi. The reaction solution was filtered to remove insoluble substances. The filtrate was dried by a spinning method to obtain a crude product, and the crude product was purified by column chromatography to obtain compound 009-15 or compound 009-16.
009-14 (51 mg, 94.16 μmol, 1 eq), palladium on carbon (0.5 mg, 10% purity, 1.00 eq) and methanol (2 mL) were added into a 100 mL hydrogenation flask, and reacted for 16 h at 45° C. under the hydrogen pressure of 45 psi. The reaction solution was filtered to remove insoluble substances. The filtrate was dried by a spinning method to obtain a crude product, and the crude product was purified by column chromatography to obtain compound 009-16 or compound 009-15.
009-15 LCMS: MS (ESI) m/z: 544.3 [M+1]$^+$
009-16 LCMS: MS (ESI) m/z: 544.3 [M+1]$^+$ Step 10: Synthesis of Compounds 009, 010, 011 and 012

009-15 (51 mg, 94.16 μmol, 1 eq) was separated in a chiral column to obtain compound 009 and compound 010. Separation condition were as below: column: DAICEL CHIRALPAK IC (250 mm×30 mm, 10 μm); mobile phase: [A: CO$_2$, B: 0.1% ammonia water-EtOH]: B %: 50%-50%,
009 LCMS: MS (ESI) m/z: 544.5 [M+1]$^+$
010 LCMS: MS (ESI) m/z: 544.5 [M+1]$^+$
009-16 (71.0 mg, 130.60 μmol, 1 eq) was separated in a chiral column o obtain compound 011 and compound 012. Separation condition were as below: column: DAICEL CHIRALPAK AS (250 mm×30 mm, 10 μm); mobile phase: [A: CO$_2$, B: 0.1% ammonia water-methanol]: B %:40%-40%.
011 LCMS: MS (ESI) m/z: 544.5 [M+1]$^+$
012 LCMS: MS (ESI) m/z: 544.5[M+1]$^+$ Target compound 009 (SFC peak position: 2.230)

¹H NMR (400 MHz, deuterated methanol) δ ppm 1.22-1.34 (m, 2H) 1.47 (d, J=7.03 Hz, 3H) 1.64 (brd, J=4.77 Hz, 2H) 1.67-1.79 (m, 3H) 2.05-2.12 (m, 2H) 2.15 (s, 3H) 2.23 (s, 3H) 2.35 (br dd, J=19.95, 10.16 Hz, 2H) 2.65 (br s, 1H) 2.73-2.91 (m, 1H) 3.11-3.31 (m, 3H) 5.93 (br d, J=6.02 Hz, 1H) 6.48-6.76 (m, 1H) 7.57 (d, J=4.27 Hz, 1H) 7.69-7.89 (m, 2H) 8.23 (s, 1H) 8.39 (d, J=4.27 Hz, 1H)

Target compound 010 (SFC peak position: 3.943)

¹H NMR (400 MHz, deuterated methanol) δ ppm 1.30-1.37 (m, 6H) 1.62 (d, J=7.28 Hz, 3H) 1.73-1.95 (m, 7H) 2.01-2.24 (m, 4H) 2.30 (s, 2H) 2.35 (s, 2H) 2.78 (brs, 1H) 2.87-3.01 (m, 1H) 6.01-6.36 (m, 1H) 6.74 (brs, 1H) 7.71 (d, J=3.76 Hz, 1H) 7.80-8.03 (m, 2H) 8.37 (s, 1H) 8.53 (d, J=4.52 Hz, 1H)

Target compound 011 (SFC peak position: 1.763)

¹H NMR (400 MHz, deuterated methanol) δ ppm 1.22-1.34 (m, 2H) 1.47 (d, J=7.03 Hz, 3H) 1.64 (brd, J=4.77 Hz, 2H) 1.67-1.79 (m, 3H) 2.05-2.12 (m, 2H) 2.15 (s, 3H) 2.23 (s, 3H) 2.35 (br dd, J=19.95, 10.16 Hz, 2H) 2.65 (br s, 1H) 2.73-2.91 (m, 1H) 3.11-3.31 (m, 3H) 5.93 (brd, J=6.02 Hz, 1H) 6.48-6.76 (m, 1H) 7.57 (d, J=4.27 Hz, 1H) 7.69-7.89 (m, 2H) 8.23 (s, 1H) 8.39 (d, J=4.27 Hz, 1H)

Target compound 012 (SFC peak position: 4.660)

¹H NMR (400 MHz, deuterated methanol) δ ppm 1.30-1.37 (m, 6H) 1.62 (d, J=7.28 Hz, 3H) 1.73-1.95 (m, 7H) 2.01-2.24 (m, 4H) 2.30 (s, 2H) 2.35 (s, 2H) 2.78 (br s, 1H) 2.87-3.01 (m, 1H) 6.01-6.36 (m, 1H) 6.74 (br s, 1H) 7.71 (d, J=3.76 Hz, 1H) 7.80-8.03 (m, 2H) 8.37 (s, 1H) 8.53 (d, J=4.52 Hz, 1H)

Example 6

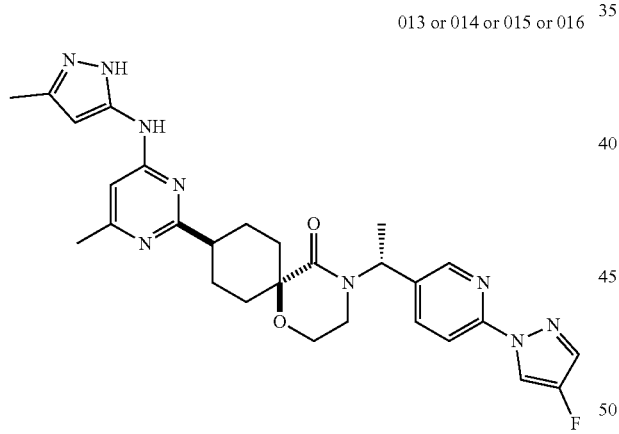

Synthetic Route:

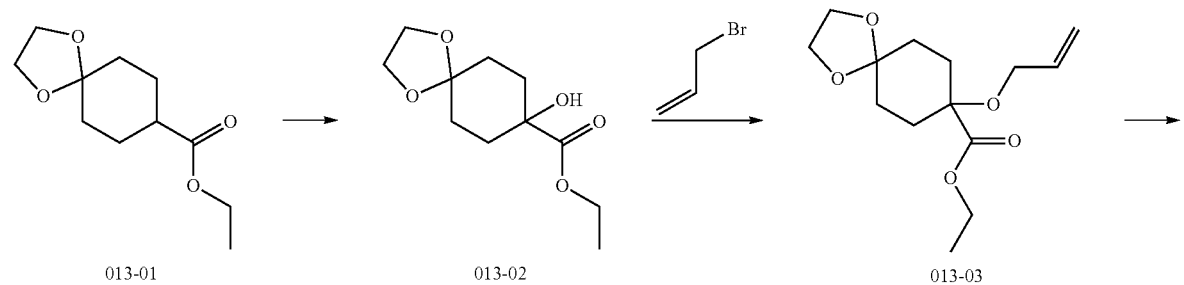

-continued
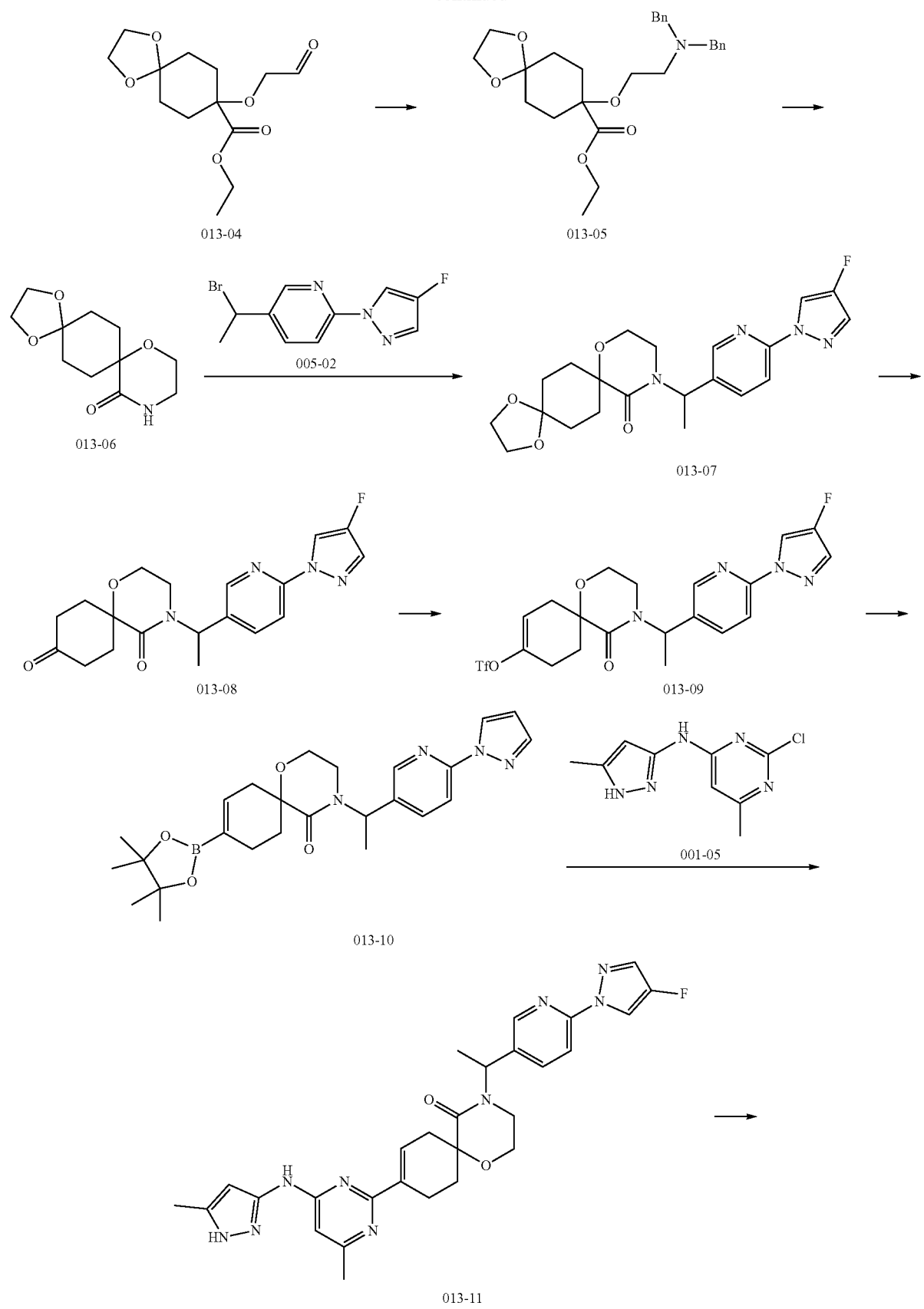

-continued
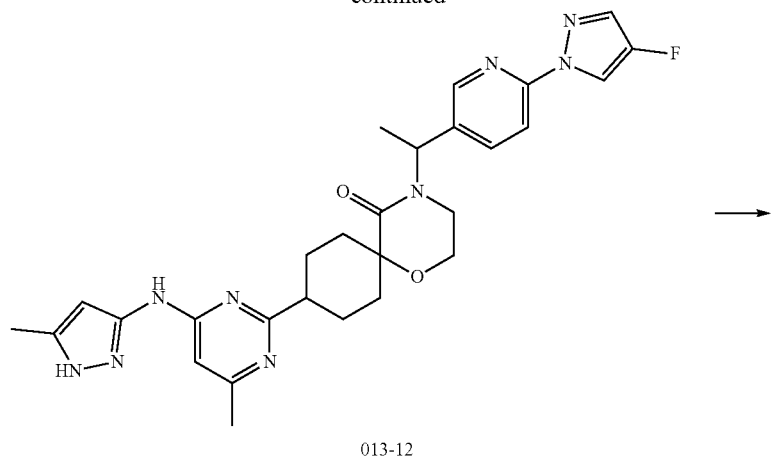
013-12
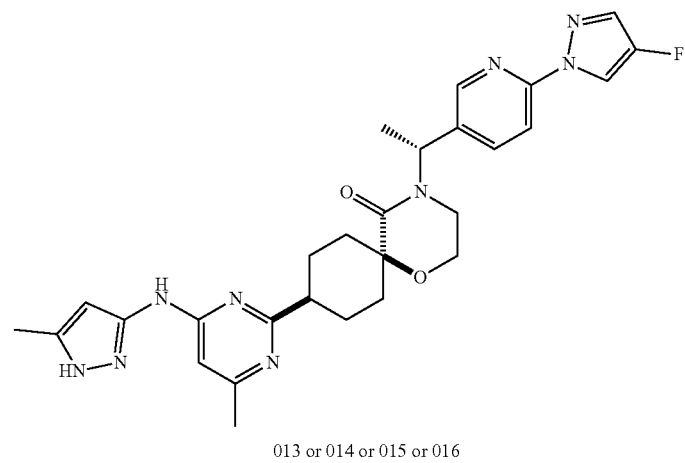
013 or 014 or 015 or 016
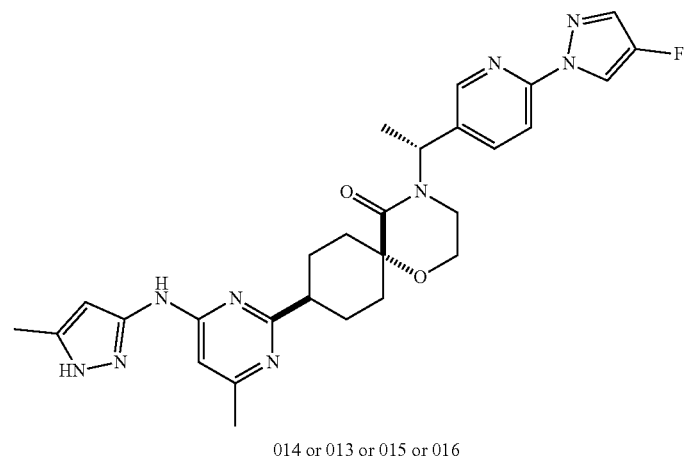
014 or 013 or 015 or 016

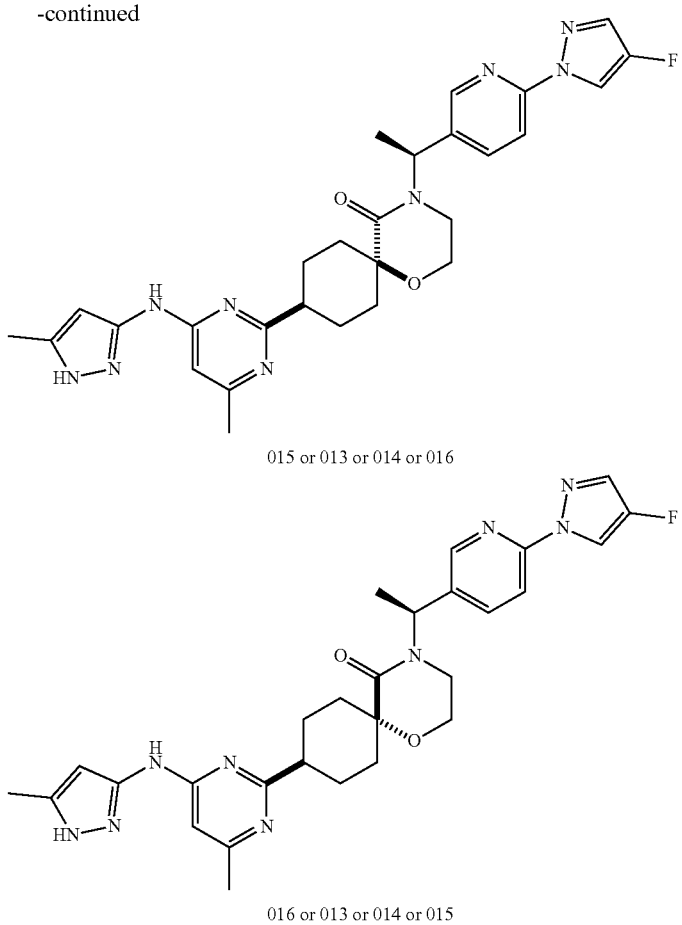

015 or 013 or 014 or 016

016 or 013 or 014 or 015

Step 1: Synthesis of Compound 013-02

Under nitrogen protection, compound 013-01 (53 g, 247.37 mmol, 1 eq) was dissolved into tetrahydrofuran (250 mL) at 0° C., lithium hexamethyldisilazide (1 M, 371.05 mL, 1.5 eq) was added, the reaction solution was stirred for 1 h, oxygen was introduced at 0° C., and then the reaction solution was stirred for 2 h. 250 mL of sodium sulfite was added into the reaction solution for quenching, the water phase was extracted for 4 times with 250 mL of ethyl acetate, and the organic phase was collected, dried with anhydrous sodium sulfate, and concentrated under reduced pressure to obtain a crude product. The obtained crude product was purified by a chromatographic column (petroleum ether/ethyl acetate=1/0 to 4/1) to obtain Compound 013-02.

Step 2: Synthesis of Compound 013-03

Compound 013-02 (9.2 g, 39.96 mmol, 1 eq) was dissolved into N,N-dimethylformamide (70 mL) at 0° C., sodium hydrogen (3.20 g, 79.91 mmol, 60% purity, 2 eq) was added, the reaction solution was stirred for 0.5 h, 3-bromopropene (14.50 g, 119.87 mmol, 3 eq) was slowly added dropwise, and then the reaction solution was heated to 20° C., and continued to stir for 1 h. The reaction solution was quenched with 50 mL of saturated ammonium chloride, and extracted with ethyl acetate (50 mL×3). The organic phases were combined, dried with anhydrous sodium sulfate, filtered, and concentrated under reduced pressure to obtain a crude product. The obtained crude product was separated and purified by column chromatography (silica gel, ethyl acetate:petroleum ether=1:20 to 1:5) to obtain compound 013-03.

Step 3: Synthesis of Compound 013-04

Compound 013-03 (20 g, 73.99 mmol, 1 eq) was dissolved into a mixture of dichloromethane (85 mL) and methanol (15 mL), sodium bicarbonate (9.32 g, 110.98 mmol, 4.32 mL, 1.5 eq) was added, the reaction solution was cooled to −78° C., ozone (3.55 g, 73.99 mmol, 1 eq) was introduced. The reaction solution was stirred for 0.5 h under a pressure of 15 psi, and then it turned blue, oxygen was continuously introduced until blue disappeared, triphenylphosphine (23.29 g, 88.78 mmol, 1.2 eq) was added, and the reaction solution was heated to 20° C. and continued to stir for 1 h. The reaction solution was directly concentrated under reduced pressure to obtain a crude product. The obtained crude product was separated and purified by column chromatography (silica gel, ethyl acetate:petroleum ether=1:10 to 1:1) to obtain Compound 013-04.

Step 4: Synthesis of Compound 013-05

N,N-dibenzylamine (4.97 g, 25.21 mmol, 4.83 mL, 0.8 eq) was dissolved into 1,2-dichloroethane (80 mL) at 0° C., sodium acetate borohydride (10.02 g, 47.27 mmol, 1.5 eq)

and compound 013-04 (13 g, 31.51 mmol, 1 eq) were added, and the reaction solution was heated to 20° C. and reacted for 1 h under stirring. The reaction solution was quenched with 50 mL of saturated sodium bicarbonate, and extracted with ethyl acetate (50 mL×3). The organic phases were combined, dried with anhydrous sodium sulfate, filtered, and concentrated under reduced pressure to obtain a crude product. The obtained crude product was separated and purified by column chromatography (ethyl acetate:petroleum ether=1:20 to 1:1) to obtain compound 013-05. $^1$H NMR (400 MHz, deuterated methanol) δ=7.37 (d, J=7.3 Hz, 4H), 7.32-7.26 (m, 4H), 7.24-7.18 (m, 2H), 4.11 (q, J=7.3 Hz, 2H), 3.92 (s, 4H), 3.65 (s, 4H), 3.40 (t, J=6.0 Hz, 2H), 2.67 (t, J=6.0 Hz, 2H), 1.99-1.86 (m, 4H), 1.76 (dt, J=5.8, 12.2 Hz, 2H), 1.61-1.52 (m, 2H), 1.19 (t, J=7.2 Hz, 3H).

Step 5: Synthesis of Compound 013-06

Compound 013-05 (10.6 g, 23.37 mmol, 1 eq) was dissolved into methanol (100 mL), palladium/carbon (1 g, 23.37 mmol, 10% purity, 1.00 eq) and potassium carbonate (6.46 g, 46.74 mmol, 2 eq) were added, hydrogen (94.42 mg, 46.74 mmol, 2 eq) was introduced, and the reaction solution was stirred for 10 h at 45° C. under the pressure of 45 psi. The reaction solution was filtered through a layer of diatomite and washed with dichloromethane, and the filtrate was concentrated under reduced pressure. The obtained residue was dissolved into a mixture of methanol (90 mL) and water (30 mL), potassium carbonate (6.46 g, 46.76 mmol, 2 eq) was added, and the reaction solution was stirred at 20° C. for 2 h. A thin-layer silica gel plate (silica gel plate, ethyl acetate:petroleum ether=1:0, $R_f$=0.30) showed that raw materials completely reacted to generate a target compound with reduced polarity. The reaction solution was concentrated under reduced pressure to remove methanol, the water phase was extracted with ethyl acetate, and organic phases were combined, dried, filtered, and concentrated under reduced pressure to obtain compound 013-06 which may be directly used in the next step without purification. $^1$H NMR (400 MHz, deuterated chloroform) δ=7.03 (br s, 1H), 3.94 (s, 4H), 3.83 (t, J=5.0 Hz, 2H), 3.39 (brt, J=6.0 Hz, 2H), 2.24-2.11 (m, 2H), 1.94 (brd, J=13.3 Hz, 2H), 1.83 (dt, J=4.1, 13.5 Hz, 2H), 1.62 (brd, J=13.1 Hz, 2H).

Step 6: Synthesis of Compound 013-07

Compound 013-06 (1.7 g, 7.48 mmol, 1 eq) was dissolved into N,N-dimethylformamide (17 mL) at 0° C., sodium hydrogen (448.79 mg, 11.22 mmol, 60% purity, 1.5 eq) was added, the reaction solution was stirred for 1 h, compound 005-02 (2.22 g, 8.23 mmol, 1.1 eq) was added, and the reaction solution was heated to 20° C. and reacted for 1 h under stirring. After being quenched with 20 mL of saturated ammonium chloride, the reaction solution was extracted with ethyl acetate (30 mL×3). The organic phases were combined, washed with saturated salt solution (20 mL×2), dried with anhydrous sodium sulfate, filtered and concentrated under reduced pressure to obtain compound 013-07.

Step 7: Synthesis of Compound 013-08

Compound 013-07 (3.12 g, 7.49 mmol, 1 eq) was dissolved into tetrahydrofuran (60 mL), hydrochloric acid aqueous solution (1 M, 74.92 mL, 10 eq) was added, the reaction solution was heated to 45° C. and reacted for 1 h under stirring. After being quenched with saturated sodium bicarbonate, the reaction solution was extracted with ethyl acetate. The organic phases were combined, dried, filtered, and concentrated under reduced pressure to obtain a crude product. The obtained crude product was separated and purified by column chromatography (silica gel column, ethyl acetate:petroleum ether=1:1 to 2:1) To obtain compound 013-08.

Step 8: Synthesis of Compound 013-09

Compound 013-08 (2 g, 5.37 mmol, 1 eq) was dissolved into tetrahydrofuran (20 mL) at −78° C., potassium hexamethyldisilazide (1 M, 7.52 mL, 1.4 eq) was slowly added, the reaction solution was stirred for 0.5 h, compound 009-08 (2.53 g, 6.44 mmol, 1.2 eq) was added, and the reaction solution was continuously stirred for 1 h. The reaction solution was quenched with 20 mL of saturated ammonium chloride at −78° C. and heated to 20° C. The water phase was extracted with ethyl acetate (50 mL×3). The organic phases were combined, washed with a saturated salt solution (20 mL×2), dried with anhydrous sodium sulfate, filtered, and concentrated under reduced pressure to obtain a crude product. The obtained crude product was separated and purified by column chromatography (silica gel, ethyl acetate:petroleum ether=1:10 to 1:3) to obtain compound 013-09.

Step 9: Synthesis of Compound 013-10

Compound 013-09 (2.48 g, 4.92 mmol, 1 eq) and bis(pinacolato)diboron (1.25 g, 4.92 mmol, 1 eq) were dissolved into dioxane (25 mL), [1,]'-bis(diphenylphosphino)ferrocene]dichloropalladium(II)dichloromethane (401.48 mg, 491.62 μmol, 0.1 eq) and potassium acetate (1.45 g, 14.75 mmol, 3 eq) were added, nitrogen was replaced for three times, and the reaction solution was heated to 110° C. and reacted for 1 h under stirring. After being cooled, the reaction solution was directly concentrated under reduced pressure to obtain a crude product. The obtained crude product was separated and purified by column chromatography (silica gel, ethyl acetate:petroleum ethe=1:10 to 1:1, $R_f$=0.80) to obtain compound 013-10.

Step 10: Synthesis of Compound 013-11

Compound 013-10 (1 g, 2.07 mmol, 1 eq) and compound 001-05 (510.06 mg, 2.28 mmol, 1.1 eq) were dissolved into dioxane (12 mL) and water (3 mL), [1,1'-bis(diphenylphosphino)ferrocene]dichloropalladium (II) (151.69 mg, 207.32 μmol, 0.1 eq) and potassium phosphate (1.32 g, 6.22 mmol, 3 eq) were added, nitrogen was replaced for three times, the reaction solution was heated to 90° C. and reacted for 1 h under stirring. The reaction solution was diluted with 200 mL of dichloromethane and washed with a saturated salt solution (30 mL×3), and the organic phase was dried with anhydrous sodium sulfate, filtered, and concentrated under reduced pressure to obtain a crude product. The obtained crude product was separated and purified by column chromatography (silica gel, dichloromethane:methanol=100:0 to 20:1) to obtain compound 013-11. LCMS: MS (ESI) m/z: 544.4 [M+1]$^+$.

Step 11: Synthesis of Compound 013-12

Compound 013-11 (500 mg, 919.80 μmol, 1 eq), palladium on carbon (100 mg, 91.98 μmol, 10% purity, 0.1 eq) and methanol (5 mL) were added into a hydrogenation flask, and heated and stirred for 16 h at 45° C. under the hydrogen (919.80 μmol) pressure of 45 psi. The reaction solution was filtered to remove palladium on carbon, and the filtrate was dried by a spinning method to obtain compound 013-12. LCMS: MS (ESI) m/z: 546.4 [M+1]+

Step 12: Synthesis of Compounds 013, 014, 015 and 016

Compound 013-12 (420 mg, 769.78 μmol, 1 eq) was separated by a chiral preparative column to obtain target compounds 013, 014, 015 and 016. Separation conditions were as below: column: DAICEL CHIRALPAK AD (250 mm×30 mm, 10 μm); mobile phase: [A: CO2, B: 0.1% ammonia water-isopropanol]: B %: 45%-45%.

Target compound: 013 (SFC peak position: 0.746)
1H NMR (400 MHz, deuterated methanol) δ ppm 1.48 (brd, J=7.13 Hz, 3H) 1.67 (br s, 2H) 1.81-2.02 (m, 6H) 2.16 (s, 3H) 2.20 (s, 3H) 2.64 (br s, 1H) 2.76-2.97 (m, 1H) 3.23-3.41 (m, 1H) 3.54-3.95 (m, 2H) 5.81 (q, J=6.92 Hz, 1H) 6.09 (br s, 1H) 6.56 (br s, 1H) 7.57 (d, J=4.13 Hz, 1H) 7.66-7.91 (m, 2H) 8.23 (s, 11H) 8.37 (d, J=4.25 Hz, 11H). LCMS: MS (ESI) m/z: 546.4 [M+1]+

Target compound: 014 (SFC peak position: 0.997)
1H NMR (400 MHz, deuterated methanol) δ ppm 1.48 (brd, J=7.13 Hz, 3H) 1.67 (brs, 2H) 1.81-2.02 (m, 6H) 2.16 (s, 3H) 2.20 (s, 3H) 2.64 (brs, 1H) 2.76-2.97 (m, 1H) 3.23-3.41 (m, 1H) 3.54-3.95 (m, 2H) 5.81 (q, J=6.92 Hz, 1H) 6.09 (brs, 1H) 6.56 (brs, 1H) 7.57 (d, J=4.13 Hz, 1H) 7.66-7.91 (m, 2H) 8.23 (s, 1H) 8.37 (d, J=4.25 Hz, 1H). LCMS: MS (ESI) m/z: 546.4 [M+1]+

Target compound: 015 (SFC peak position: 0.595)
1H NMR (400 MHz, deuterated methanol) δ ppm 1.61 (d, J=7.03 Hz, 3H) 1.65-1.81 (m, 2H) 1.91-2.12 (m, 2H) 2.23-22.37 (m, 9H) 2.91-3.07 (m, 2H) 3.37 (s, 1H) 3.42-3.52 (m, 1H) 3.74-3.98 (m, 2H) 5.93 (q, J=7.03 Hz, 1H) 6.16-6.90 (m, 2H) 7.70 (d, J=4.02 Hz, 1H) 7.83-7.98 (m, 2H) 8.38 (s, 1H) 8.51 (d, J=4.27 Hz, 11H). LCMS: MS (ESI) m/z: 546.4 [M+1]+

Target compound: 016 (SFC peak position: 0.610)
1H NMR (400 MHz, deuterated methanol) δ ppm 1.61 (d, J=7.03 Hz, 3H) 1.65-1.81 (m, 2H) 1.91-2.12 (m, 2H) 2.23-22.37 (m, 9H) 2.91-3.07 (m, 2H) 3.37 (s, 1H) 3.42-3.52 (m, 1H) 3.74-3.98 (m, 2H) 5.93 (q, J=7.03 Hz, 1H) 6.16-6.90 (m, 2H) 7.70 (d, J=4.02 Hz, 11H) 7.83-7.98 (m, 2H) 8.38 (s, 11H) 8.51 (d, J=4.27 Hz, 1H). LCMS: MS (ESI) m/z: 546.4 [M+1]+

Example 7

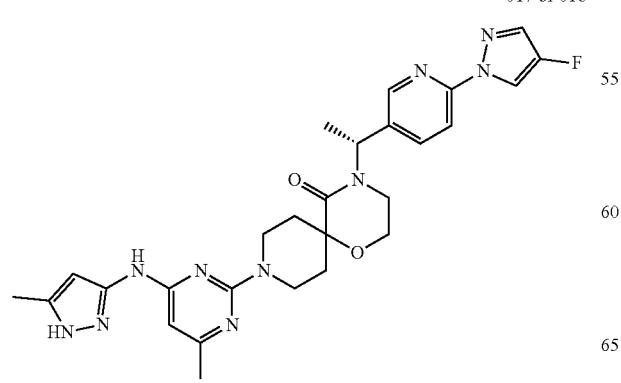

017 or 018

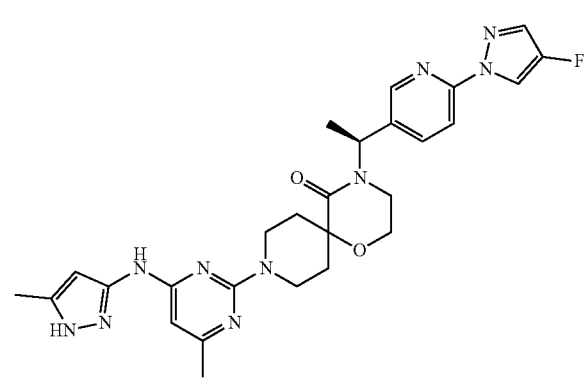

018 or 017

Synthetic Route:

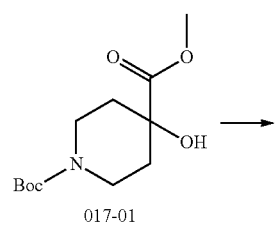

017-01

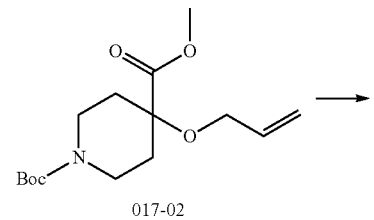

017-02

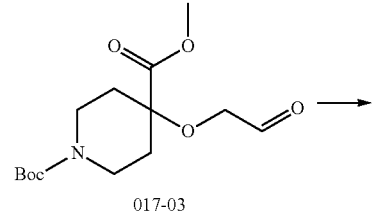

017-03

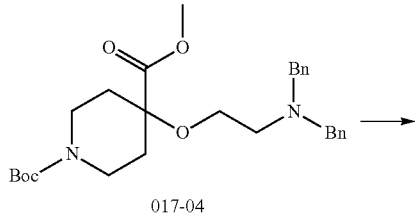

017-04

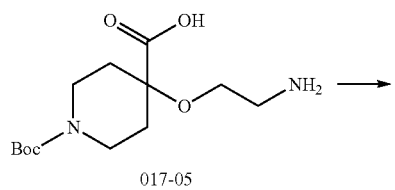

017-05

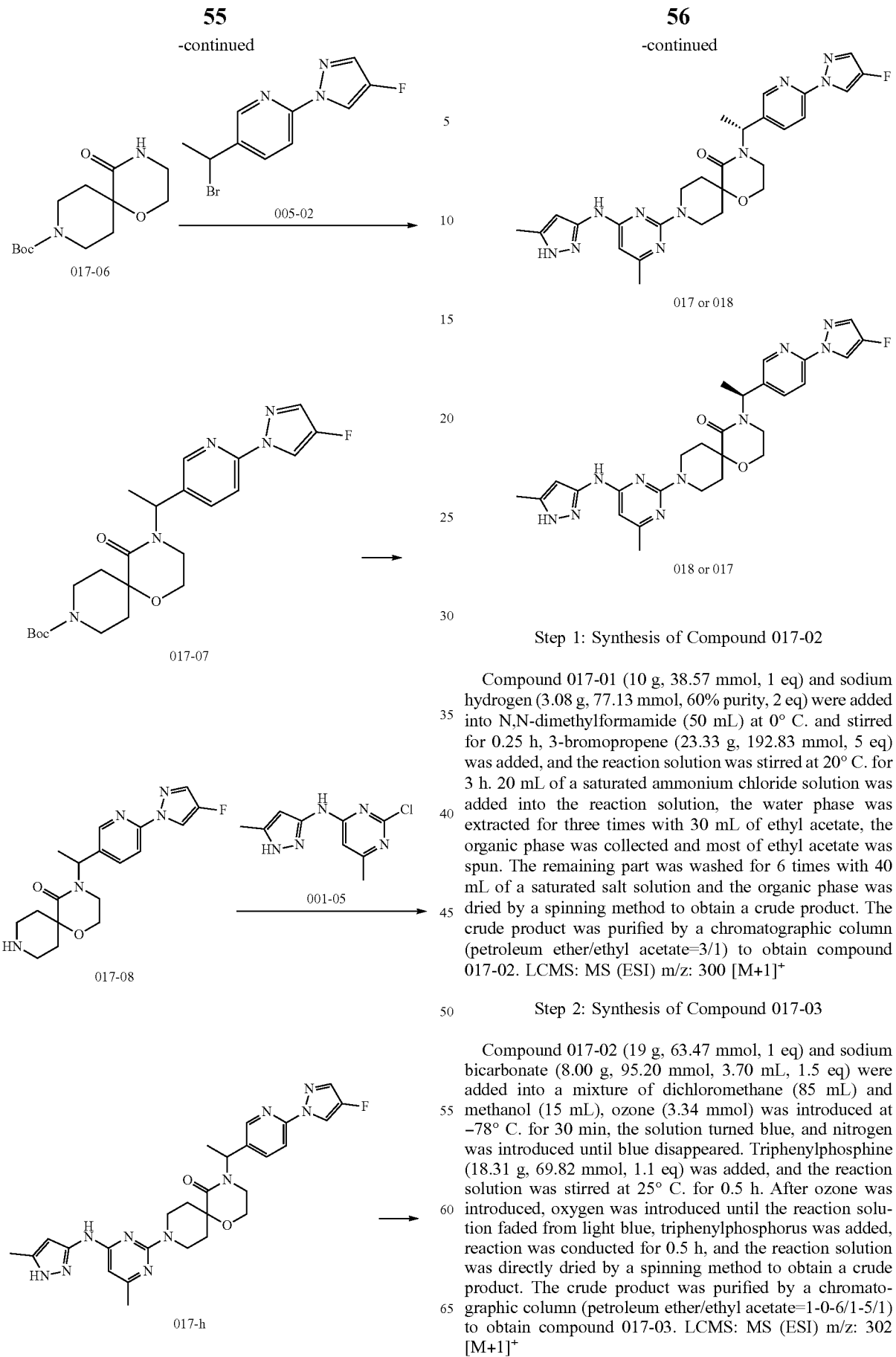

Step 1: Synthesis of Compound 017-02

Compound 017-01 (10 g, 38.57 mmol, 1 eq) and sodium hydrogen (3.08 g, 77.13 mmol, 60% purity, 2 eq) were added into N,N-dimethylformamide (50 mL) at 0° C. and stirred for 0.25 h, 3-bromopropene (23.33 g, 192.83 mmol, 5 eq) was added, and the reaction solution was stirred at 20° C. for 3 h. 20 mL of a saturated ammonium chloride solution was added into the reaction solution, the water phase was extracted for three times with 30 mL of ethyl acetate, the organic phase was collected and most of ethyl acetate was spun. The remaining part was washed for 6 times with 40 mL of a saturated salt solution and the organic phase was dried by a spinning method to obtain a crude product. The crude product was purified by a chromatographic column (petroleum ether/ethyl acetate=3/1) to obtain compound 017-02. LCMS: MS (ESI) m/z: 300 [M+1]$^+$

Step 2: Synthesis of Compound 017-03

Compound 017-02 (19 g, 63.47 mmol, 1 eq) and sodium bicarbonate (8.00 g, 95.20 mmol, 3.70 mL, 1.5 eq) were added into a mixture of dichloromethane (85 mL) and methanol (15 mL), ozone (3.34 mmol) was introduced at −78° C. for 30 min, the solution turned blue, and nitrogen was introduced until blue disappeared. Triphenylphosphine (18.31 g, 69.82 mmol, 1.1 eq) was added, and the reaction solution was stirred at 25° C. for 0.5 h. After ozone was introduced, oxygen was introduced until the reaction solution faded from light blue, triphenylphosphorus was added, reaction was conducted for 0.5 h, and the reaction solution was directly dried by a spinning method to obtain a crude product. The crude product was purified by a chromatographic column (petroleum ether/ethyl acetate=1-0-6/1-5/1) to obtain compound 017-03. LCMS: MS (ESI) m/z: 302 [M+1]$^+$

Step 3: Synthesis of Compound 017-04

Compound 017-03 (14.5 g, 48.12 mmol, 1 eq) and N,N-dibenzylamine (7.59 g, 38.50 mmol, 7.37 mL, 0.8 eq) were dissolved into dichloroethane (70 mL) at 20° C., sodium acetate borohydride (12.24 g, 57.74 mmol, 1.2 eq) was added, and the reaction solution was stirred for 5 min. 20 mL of saturated ammonium chloride was added into the reaction solution for quenching, the resulting reaction solution was extracted with dichloromethane (40 mL×2). The organic phases were combined, dried with anhydrous sodium sulfate, filtered, and concentrated under reduced pressure to obtain a crude product. The obtained crude product was purified by a chromatographic column (petroleum ether/ethyl acetate=1/0 to 5/1) to obtain compound 017-04. LCMS: MS (ESI) m/z: 483 [M+1]$^+$

Step 4: Synthesis of Compound 017-05

Compound 017-04 (6.1 g, 12.64 mmol, 1 eq) was added into a hydrogenation flask containing methanol (60 mL), palladium/carbon (0.6 g, 10%) was added, and air in the hydrogenation flask was replaced with argon for 4 times. Hydrogen (45 psi) was continuously introduced, and the reaction solution was stirred at 45° C. for 12 h. After the reaction solution was filtrated with diatomite, the diatomite was washed with methanol for 3 times, and the organic phase was collected and dried by a spinning method to obtain a crude product. The crude product was added into methanol (30 mL) and water (10 mL), potassium carbonate (6.37 g, 46.10 mmol, 3 eq) and palladium/carbon (1.2 g, 10% purity) were added, the air was exchanged, and the reaction was conducted at 25° C. for 3 h under hydrogen (45 psi). The reaction solution was filtered with diatomite, and the diatomite was washed for 3 times with 20 mL of methanol. The organic phase was collected and dried by a spinning method to obtain a crude product. The obtained crude product was added into a hydrogenation flask containing methanol (50 mL), the air in the hydrogenation flask was replaced with argon, and reaction solution was stirred for 24 h at 60° C. under hydrogen (50 psi). The reaction solution was filtered with diatomite, the diatomite was washed 3 times with 20 mL of methanol, and the organic phase was collected and dried by a spinning method to obtain compound 017-05.

Step 5: Synthesis of Compound 017-06

Compound 017-05 (1.5 g, 5.20 mmol, 1 eq) was added into N,N-dimethylformamide (10 mL), diisopropylethylamine (2.02 g, 15.61 mmol, 2.72 mL, 3 eq) and propyl phosphoric anhydride (8.28 g, 13.01 mmol, 7.73 mL, 50% purity, 2.5 eq) were added, and the reaction solution was stirred at 25° C. for 0.5 h. 2 mL of 1 M hydrochloric acid was added into the reaction solution, 5 mL of water was added, and the water phase was extracted with 10 mL of ethyl acetate for 3 times. The organic phase was collected and washed with 20 mL of a saturated salt solution for 4 times, dried with anhydrous sodium sulfate, and dried by a spinning method to obtain compound 017-06.

Step 6: Synthesis of Compound 017-07

Compound 017-06 (1.2 g, 4.44 mmol, 1 eq) was dissolved into N,N-dimethylfomamide (10 mL) at 0° C., sodium hydrogen (213.06 mg, 5.33 mmol, 60% purity, 1.2 eq) was added, the reaction solution was stirred for 0.2 h, compound 005-02 (1.26 g, 4.66 mmol, 1.05 eq) was added, and the reaction solution was heated to 20° C. and continued to stir for 0.5 h. The reaction solution was poured into 10 mL of water, and filtered to obtain filter cake. The filter cake was washed with 10 mL of water, and then washed with 5 mL of petroleum ether. The filter cake was collected, and dried by a spinning method under reduced pressure to obtain compound 017-07.

Step 7: Synthesis of Compound 017-08

Compound 017-07 (1.9 g, 4.13 mmol, 1 eq) was added into dichloromethane (20 mL), trifluoroacetic acid (6.16 g, 54.03 mmol, 4 mL, 13.07 eq) was added, and the reaction solution was stirred at 25° C. for 0.5 h. The reaction solution was directly dried by a spinning method, 20 mL of dichloromethane was added, and then continued to dry by a spinning method, and the operations were repeated for 3 times. Trifluoroacetate of compound 017-08 was obtained.

Step 8: Synthesis of Compound 017-h

The trifluoroacetate of compound 017-08 (787.08 mg, 3.52 mmol, 0.85 eq) and compound 001-05 (1.96 g, 4.14 mmol, 1 eq, TFA) were added into n-butanol (10 mL), diisopropylethylamine (1.61 g, 12.42 mmol, 2.16 mL, 3 eq) was added, and the reaction solution was heated and stirred at 130° C. for 16 h. The reaction solution was directly dried by a spinning method to obtain a crude product. The crude product was purified by a chromatographic column (dichloromethane/methanol=1/0-4% methanol), and purified by high performance chromatography (column: VenusilASB Phenyl 150×30 mm×5 μm; mobile phase: [water (0.05% hydrochloric acid)-acetonitrile]; acetonitrile %: 30%-60%, 9 min) to obtain compound 017-h. LCMS: MS (ESI) m/z: 547 [M+1]$^+$

Step 9: Synthesis of Compound 017 or 018

The compound 017-h (0.75 g, 1.37 mmol, 1 eq) was subjected to chiral resolution (column: DAICEL CHIRALPAK AS (250 mm×50 mm, 10 μm); mobile phase: [A: CO$_2$, B: 0.1% ammonia water-ethanol]; B %: 50%-50%) to obtain compound 017 and compound 018.

Target compound: 017 (SFC peak position: 3.645)

$^1$H NMR (400 MHz, deuterated methanol) δ ppm 1.62 (d, J=6.8 Hz, 3H) 1.86-1.93 (m, 2H) 2.09-2.13 (m, 2H) 2.22 (s, 3H) 2.28 (s, 3H) 3.02-3.20 (m, 3H) 3.46-3.48 (m, 1H) 3.87-3.97 (m, 2H) 4.58-4.61 (m, 2H) 4.90 (m, 1H) 5.89-5.94 (m, 1H) 6.11-6.22 (m, 1H) 7.70 (d, J=4 Hz, 1H) 7.87-7.96 (m, 2H) 8.38 (s, 1H) 8.52 (d, J=4.4 Hz, 1H). LCMS: MS (ESI) m/z: 547 [M+1]$^+$ Target compound: 018 (SFC peak position: 4.906)

$^1$H NMR (400 MHz, deuterated methanol) δ ppm 1.62 (d, J=6.8 Hz, 3H) 1.86-1.93 (m, 2H) 2.09-2.13 (m, 2H) 2.22 (s, 3H) 2.28 (s, 3H) 3.02-3.20 (m, 3H) 3.46-3.48 (m, 1H) 3.87-3.97 (m, 2H) 4.58-4.61 (m, 2H) 4.90 (m, 1H) 5.89-5.94 (m, 1H) 6.11-6.22 (m, 1H) 7.70 (d, J=4 Hz, 1H) 7.87-7.96 (m, 2H) 8.38 (s, 1H) 8.52 (d, J=4.4 Hz, 1H). LCMS: MS (ESI) m/z: 547 [M+1]$^+$ Biological Test Data:

Experimental Example 1: Evaluation on Inhibitory Activity In-Vitro of Wild-Type and V804M Mutant Kinases $^{33}$P isotope-labeled kinase activity test (Reaction Biology Corp) was used to determine $IC_{50}$ value so as to evaluate an inhibitory ability of a test compound on human wild-type, V804M and V804L mutant RET.

Buffer solution condition: 20 mM 4-(2-hydroxyethyl)piperazine-1-ethanesulfonic acid (Hepes) (pH 7.5), 10 mM $MgCl_2$, 1 mM 1,2-bis[2-[bis(carboxymethyl)amino]ethoxy]ethane (EGTA), 0.02% polyoxyethylene lauryl ether (Brij35), 0.02 mg/mL bovine serum albumin (BSA), 0.1 mM of $Na_3VO_4$, 2 mM dithiothreitol (DTT) and 1% DMSO.

Compound treatment: the compound to be tested was dissolved in 100% DMSO, and then the obtained solution was continuously diluted with DMSO by using Integra Viaflo Assist until a specific concentration was obtained.

Test procedures: a substrate was dissolved in the newly prepared buffer solution, a kinase to be tested was added therein, and the obtained solution was gently and evenly mixed. DMSO solution in which a compound to be test was dissolved was added in the above evenly mixed reaction solution by using an acoustic technology (Echo 550), and then incubated for 20 minutes at room temperature. The concentrations of the compounds in the reaction solutions were 3 μM, 1 μM, 0.333 μM, 0.111 μM, 0.0370 μM, 0.0123 μM, 4.12 nM, 1.37 nM, 0.457 nM and 0.152 nM, respectively. After incubation for 15 min, $^{33}$P-ATP (activity of 0.01 μCi/μL, $K_m$ concentration) was added and the reaction was started. After the reaction was conducted at room temperature for 120 min, radioactivity was detected by a filter binding method. Kinase activity data was expressed by comparing the kinase activity of the compound to be tested with the kinase activity of a blank group (containing only DMSO). The $IC_{50}$ value was obtained by curve fitting with Prism4 software (GraphPad). The experimental results were shown in Table 1.

TABLE 1

In-vitro screening test results of the compounds of the present disclosure

| Compound | $IC_{50}$ (nM) | | |
|---|---|---|---|
| | Wild-type | V804M | V804L |
| 001-h | 92.99 | 128.70 | ND |
| 003-h | 73.87 | 133.60 | ND |
| 005-h | 3.00 | 13.02 | ND |
| 007 | 68.88 | 116.30 | ND |
| 008 | 0.36 | 0.71 | ND |
| 009 | 91.03 | ND | ND |
| 010 | 119.9 | ND | ND |
| 011 | 233.60 | ND | ND |
| 012 | 0.90 | 1.06 | 0.47 |
| 013 | 46.7 | ND | ND |
| 014 | 1.12 | 4.1 | 1.23 |
| 015 | 48.30 | ND | ND |
| 016 | 75.23 | ND | ND |
| 017 | 70.32 | 74.30 | ND |
| 018 | 1.29 | 1.97 | 1.23 |

Note:
"ND" refers to that no detection was performed.

Conclusion: The compounds of the present disclosure showed relatively good inhibitory activity on the wild-type, V804M and V804L mutant RET.

Experimental Example 2: Pharmacokinetic Evaluation on Compounds

Experiment objective: to test the pharmacokinetic of compound in mice

Experiment material: CD-1 mice (male)

Experiment operations: the pharmacokinetic characteristics of rodents after intravenous injection and oral administration of the compounds were obtained by using a standard scheme. In the experiment, candidate compounds were formulated into clear solutions, and mice were administrated by a single intravenous injection and oral administration. The solvent of the intravenous injection and oral administration was 10% PEG400 (polyethylene glycol 400)+90% (10% hydroxypropyl-β-cyclodextrin). The whole blood samples were collected within 24 hours. All the blood samples were added respectively into labeled plastic centrifuge tubes in which 0.5 M $K_2$-EDTA anticoagulants were pre-added. The blood samples were collected, and centrifuged at 3,000 g for 10 min at 4° C. The supernatant plasma was collected by absorbing and quickly placed in dry ice to keep at −20° C. or lower. Blood concentrations were quantitatively analyzed by using an LC-MS/MS analysis method, and pharmacokinetic parameters, such as peak concentration, peak time, clearance rate, half-life, area under drug concentration-time curve, bioavailability, etc. were calculated.

The experiment results were shown in Table 2.

TABLE 2

Pharmacokinetic test results of the compounds of the present disclosure

| Samples to be Test (Compounds) | Injection Administration (2 mpk) | | | Oral Administration (10 mpk) | |
|---|---|---|---|---|---|
| | Clearance Rate (mL/min/kg) | Half-life $T_{1/2}$ (h) | Integrated Concentration AUC (nM · hr) | Integrated Concentration AUC (nM · hr) | Bioavailability F (%) |
| Compound 014 | 1.65 | 2.53 | 16414 | 49619 | 53.7 |

TABLE 2-continued

Pharmacokinetic test results of the compounds of the present disclosure

| Samples to be Test (Compounds) | Injection Administration (2 mpk) | | | Oral Administration (10 mpk) | |
|---|---|---|---|---|---|
| | Clearance Rate (mL/min/kg) | Half-life $T_{1/2}$ (h) | Integrated Concentration AUC (nM · hr) | Integrated Concentration AUC (nM · hr) | Bioavailability F (%) |
| Compound 018 | 6.55 | 2.56 | 9301 | 27723 | 59.7 |

Conclusion: The pharmacokinetic of the compounds of the present disclosure in mice have good pharmacokinetic indexes.

Experimental Example 3: Evaluation on Efficacy of Compounds in Ba/F3 KIF5B-RET-V804L Tumor Cell Xenograft Model 1. Experiment Objective:

An engineered cell line Ba/F3 KIF5B-RET-V804L tumor cell xenograft model was established in NPSG mice, and efficacy of drugs to be tested alone on the xenograft model of NPSG mice was verified.

2. Experiment Design:

1) Ba/F3 KIF5B-RET-V804L cells were resuscitated and cultured in vitro to obtain $5 \times 10^7$ cells.

2) Forty-five 6-8 week old female mice were adaptively fed for 1 week and weighed.

3) Ba/F3 KIF5B-RET-V804L tumor cells were subcutaneously inoculated into the right scapula position of the mice so as to establish the engineered cell line Ba/F3 KIF5B3-RET-V804L tumor cell xenograft model. Inoculation conditions were as follows: (see Table 3)

TABLE 3

Inoculation information

| Animal Strain | Number of Animals | Type of Inoculation Cells | Inoculation Position | Inoculation Cell Amount (Cell) | Volume of Inoculation Cell Suspension (mL) | Total Amount of Needed Cells |
|---|---|---|---|---|---|---|
| NPSG | 45 | Ba/F3 KIF5B-RET-V804L | Subcutaneous tissue | $1 \times 10^6$ | 0.1 mL | $5 \times 10^7$ |

4) After inoculation, the volume and weight of tumors were measured once a week. When the average tumor volume reached 124.5 mm³, mice with the tumor volume between 82.9 mm³ and 145.4 mm³ were selected and randomly grouped according to the volume and weight of tumors with 6 mice in each group. The administration was started immediately after the grouping. The start date of the administration was recorded as day 0. Administration and grouping information were seen in Table 4.

TABLE 4

Grouping and administration information

| Group | Number of Animals | Sample for Test | Administration Dosage (m/kg) | Administration Route | Administration Amount μL/g | Administration Period |
|---|---|---|---|---|---|---|
| 1 | 6 | Blank Control | NA | p.o. | 10 | Day 0-Day 9 BID |
| 2 | 6 | Compound 014 | 10 | p.o. | 10 | Day 0-Day 9 BID |
| 3 | 6 | Compound 018 | 10 | p.o. | 10 | Day 0-Day 9 BID |

Note:
NA represents no administration; Day 0-Day 9 represents from day 0 to day 9.

5) After the administration was started, the mice were continuously administrated for 9 days, and the body weight and tumor volume of the mice were measured on day 3, day 6, and day 9.

6) Data statistics were analyzed by one-way ANOVA. Variance homogeneity difference of data was firstly detected. If there was no difference in the variance homogeneity, an LSD method was used for analysis; and if there was a difference in the variance homogeneity, Dunnett's T3 was selected for data analysis. All data were analyzed by using SPSS 17.0. A p value less than 0.05 was considered a significant difference.

3. Experimental Results 3.1 Body Weight

The average body weights of each group at different time points were shown in Table 5.

TABLE 5

Body weight changes of mice in each group in experiment

| Number of Day | Blank Control | Compound 014 10 mg/kg | Compound 018 10 mg/kg |
|---|---|---|---|
| 0 | 18.7 ± 0.5 | 19.5 ± 0.53 | 18.6 ± 0.49 |
| 3 | 19.6 ± 0.52 | 20.3 ± 0.72 | 18.8 ± 0.48 |
| 6 | 20 ± 0.63 | 20.5 ± 0.72 | 18.6 ± 0.87 |
| 9 | 20.4 ± 0.45 | 20.3 ± 0.84 | 19 ± 0.64 |

3.2 Inhibition of Tumor Growth

Inhibition of tumor growth in each group was shown in Table 6.

TABLE 6

Tumor-inhibition effect of mice in each group

| Treatment | Tumor Volume on Day 0 (mm$^3$)$^a$ | Tumor Volume on Day 9 (mm$^3$)$^a$ | TGI (%) | ΔVAC (%) | P value |
|---|---|---|---|---|---|
| Blank Control Compound | 126.3 ± 4.66 | 827.8 ± 44.98 | / | / | / |
| 014 10 mg/kg | 123.8 ± 7.2 | 84.8 ± 6.25 | 106% | −6% | <0.001 |
| Compound 018 10 mg/kg | 125 ± 3.96 | 75.5 ± 7.11 | 107% | −7% | <0.001 |

Note:
$^a$means an average nunber ± standard error;
b means that the data was analyzed by using One-way ANOVA, and a Dunnetts T3 method was used for post-mortem analysis due to uneven variance;
TGI represents tumor growth inhibition rate and its value is 1-ΔT/ΔC;
ΔT represents increased tumor volume in the experimental group;
ΔC represents increased tumor volume in the control group.

Conclusion: in the engineered cell line Ba/F3 KIF5B-RET-V804L xenograft model of mice, the compounds of the present disclosure showed relatively strong efficacy for 9 consecutive administration days.

Experimental Example 4: Evaluation on Efficacy of Compounds in Engineered Cell Line Ba/F3 KIF5-RET Xenograft Model of Female NPSG Mice 1. Experiment Objective:

To verify efficacy of drugs to be tested alone on the engineered cell line Ba/F3 KIF5B-RET xenograft model of NPSG mice.

2. Experiment Design:

1) Ba/F3 KIF5B-RET cells were resuscitated and cultured in vitro to obtain 4×10$^7$ cells.

2) Sixty 6-8 week old female NPSG mice were adaptively fed for one week and weighed.

3) The Ba/F3 KIF5B-RET cells were subcutaneously inoculated on right scapula of mice according to the inoculation conditions obtained in the pre-test (see Table 7) to establish the Ba/F3 KIF5B-RET tumor cell xenograft model of NPSG mice.

TABLE 7

Inoculation information

| Animal Strain | Number of Animals | Type of Inoculation Cells | Inoculation Position | Inoculation Amount (Cell) | Volume of Inoculation Cell Suspension (mL) | Total Amount of Needed Cells |
|---|---|---|---|---|---|---|
| NPSG | 60 | Ba/F3 KIF5B-RET | Subcutaneous tissue | 1 × 10$^6$ | 0.1 mL | 6 × 10$^7$ |

4) After inoculation, the volume and weight of tumors were measured once a week. When the average tumor volume reached 104 mm$^3$, mice were randomly grouped according to the volume and weight of tumors with 6 mice in each group. The administration was started immediately after the grouping. The start date of the administration was recorded as day 0. Administration and grouping information were shown in Table 8.

TABLE 8

Grouping and administration information

| Group | Number of Animals | Sample for Test | Administration Dosage (m/kg) | Administration Route | Administration Amount μL/g | Administration Period |
|---|---|---|---|---|---|---|
| 1 | 6 | Blank Control | NA | p.o. | 10 | Day 0-Day 10 BID |
| 2 | 6 | Compound 014 | 10 | p.o. | 10 | Day 0-Day 10 BID |
| 3 | 6 | Compound 018 | 10 | p.o. | 10 | Day 0-Day 10 BID |
| 4 | 6 | Compound 018 | 20 | p.o. | 10 | Day 0-Day 10 BID |

Note:
NA represents no administration; Day 0-Day 10 represents from day 0 to day 10.

5) After administration was started, the body weight and tumor volume of the mice were measured respectively on the day 0, day 3, day 6, and day 10.

6) For the experiment of two groups, a T-Test analysis method was used. For a comparison of three or more groups, One-Way ANOVA was used for analysis. For comparing potential synergistic effects, Two-Way ANOVA was used for analysis. All data were analyzed by using SPSS 17.0. A p value less than 0.05 was considered to be a significant difference, and a p value less than 0.01 was considered to be a very significant difference.

3. Experimental Results 3.1 Body Weight

The average body weights of each group at different time points were shown in Table 9.

TABLE 9

Body weight changes in each group

| Number of Days | Blank Control | Compound 014 10 mg/kg | Compound 018 10 mg/kg | Compound 018 20 mg/kg |
|---|---|---|---|---|
| 0 | 17.2 ± 0.26 | 18 ± 0.57 | 17.7 ± 0.47 | 17.6 ± 0.58 |
| 3 | 18 ± 0.36 | 18.5 ± 0.47 | 18.2 ± 0.51 | 18.1 ± 0.56 |
| 6 | 18.4 ± 0.24 | 18.5 ± 0.75 | 18.5 ± 0.57 | 18.3 ± 0.53 |
| 10 | 19.6 ± 0.31 | 18.6 ± 0.62 | 17.7 ± 0.86 | 18.5 ± 0.63 |

3.2 Inhibition of Tumor Growth

Inhibition of tumor growth in each group was shown in Table 10.

TABLE 10

Tumor-inhibition effect of drugs in each group

| Treatment | Tumor Volume on Day 0 (mm³)[a] | Tumor Volume on Day 9 (mm³)[a] | TGI (%) | ΔVAC (%) | P value[b] |
|---|---|---|---|---|---|
| Blank Control | 105.8 ± 7.75 | 1063.5 ± 65.21 | / | / | / |
| 014 10 mg/kg Compound | 102.3 ± 7.72 | 116.6 ± 10.77 | 99% | 1% | <0.001 |
| 018 10 mg/kg Compound | 106.3 ± 7.14 | 205.1 ± 29.87 | 90% | 10% | <0.001 |
| 018 20 mg/kg | 102.2 ± 7.09 | 32.8 ± 6.81 | 107% | −7% | <0.001 |

Note:
[a] means an average number ± standard error;
[b] means that the data was analyzed by using One-way ANOVA and a Dunnett's T3 method was used for post-mortem analysis due to uneven variance;
TGI represents tumor growth inhibition rate and its value is 1-ΔT/ΔC;
ΔT represents increased tumor volume in the experimental group;
ΔC represents increased tumor volume in the control group.

Conclusion: in the engineered cell line Ba/F3 KIF5B-RET xenograft model of mice, the compounds of the present disclosure showed relatively strong efficacy for 10 consecutive administration days.

The invention claimed is:

1. A compound of a formula (II) or a pharmaceutically acceptable salt thereof,

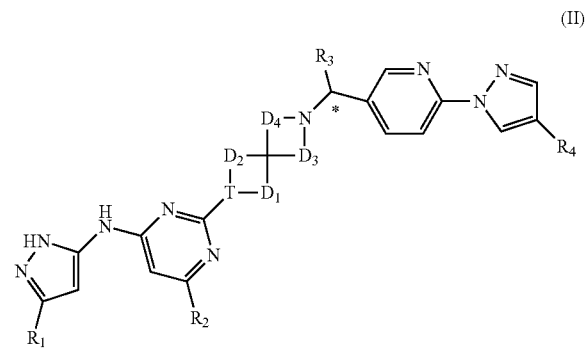

wherein,
T is selected from CH and N;
$R_1$ is selected from H, F, Cl, Br, I and $C_{1-6}$ alkyl, and the $C_{1-6}$ alkyl is optionally substituted with 1, 2 or 3 $R_a$;
$R_2$ is selected from H, F, Cl, Br, I and $C_{1-6}$ alkyl, and the $C_{1-6}$ alkyl is optionally substituted with 1, 2 or 3 $R_b$;
$R_3$ is selected from H, F, Cl, Br, I and $C_{1-6}$ alkyl, and the $C_{1-6}$ alkyl is optionally substituted with 1, 2 or 3 $R_c$;

$R_4$ is selected from H, F, Cl, Br, I, OH, $NH_2$ and $C_{1-3}$ alkyl, and the $C_{1-3}$ alkyl is optionally substituted with 1, 2 or 3 $R_d$;

$D_1$ is —$CH_2CH_2$— optionally substituted with 1, 2 or 3 $R_e$;

$D_2$ is —$CH_2CH_2$— optionally substituted with 1, 2 or 3 $R_f$;

$D_3$ is selected from —$CH_2$— and

and the —$CH_2$— is optionally substituted with 1 or 2 $R_g$;

$D_4$ is selected from —$CH_2CH_2$—, —$CH_2CH_2CH_2$— and —O—$CH_2CH_2$—, each of which is optionally substituted with 1, 2 or 3 $R_h$;

$R_a$, $R_b$, $R_c$ and $R_d$ are independently selected from F, Cl, Br, I, OH, $NH_2$ and $CH_3$;

$R_e$, $R_f$, $R_g$ and $R_h$ are independently selected from F, Cl, Br, I and $CH_3$;

a carbon atom with "*" is a chiral carbon atom, which is present in a form of (R) or (S) single enantiomer or in an enriched enantiomeric form.

2. The compound or the pharmaceutically acceptable salt thereof according to claim 1, wherein $R_1$ is selected from H, F, Cl, Br, I, $CH_3$, $CH_2CH_3$,

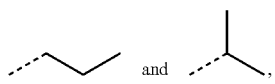

and the $CH_3$, $CH_2CH_3$,

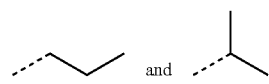

and are optionally substituted with 1, 2 or 3 $R_a$.

3. The compound or the pharmaceutically acceptable salt thereof according to claim 2, wherein $R_1$ is selected from H, F, Cl, Br, I, $CH_3$, $CF_3$, $CH_2CH_3$, $CH_2CF_3$,

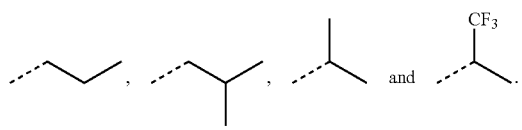

4. The compound or the pharmaceutically acceptable salt thereof according to claim 3, wherein $R_1$ is $CH_3$.

5. The compound or the pharmaceutically acceptable salt thereof according to claim 1, wherein $R_2$ is selected from H, F, Cl, Br, I, $CH_3$, $CH_2CH_3$,

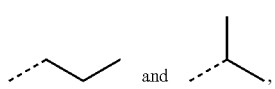

and the $CH_3$, $CH_2CH_3$,

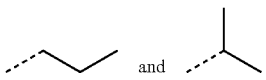

and are optionally substituted with 1, 2 or 3 $R_b$.

6. The compound or the pharmaceutically acceptable salt thereof according to claim 5, wherein $R_2$ is selected from H, F, Cl, Br, I, $CH_3$, $CF_3$, $CH_2CH_3$, $CH_2CF_3$,

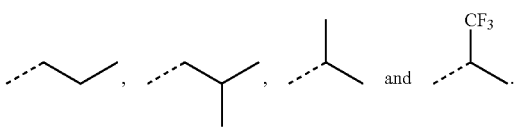

7. The compound or the pharmaceutically acceptable salt thereof according to claim 6, wherein $R_2$ is $CH_3$.

8. The compound or the pharmaceutically acceptable salt thereof according to claim 1, wherein $R_3$ is selected from H, F, Cl, Br, I, $CH_3$, $CH_2CH_3$,

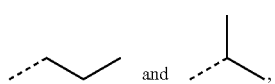

and the $CH_3$, $CH_2CH_3$,

are optionally substituted with 1, 2 or 3 $R_c$.

9. The compound or the pharmaceutically acceptable salt thereof according to claim 8, wherein $R_3$ is selected from H, F, Cl, Br, I, $CH_3$, $CF_3$, $CH_2CH_3$, $CH_2CF_3$,

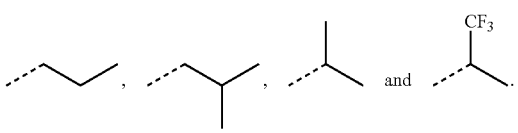

10. The compound or the pharmaceutically acceptable salt thereof according to claim 9, wherein $R_3$ is $CH_3$.

11. The compound or the pharmaceutically acceptable salt thereof according to claim 1, wherein $R_4$ is selected from H, F, Cl, Br, I, $CH_3$, $CF_3$, $CH_2CH_3$, $CH_2CF_3$,

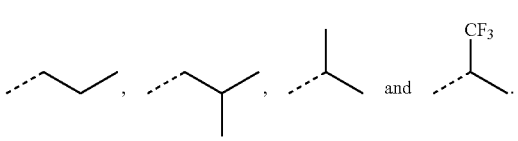

12. The compound or the pharmaceutically acceptable salt thereof according to claim 11, wherein $R_4$ is F.

13. The compound or the pharmaceutically acceptable salt thereof according to claim 1, wherein the structure unit
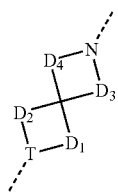
is selected from
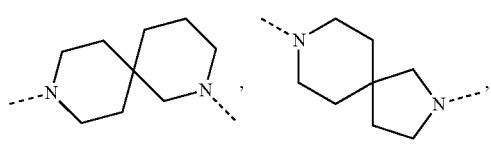
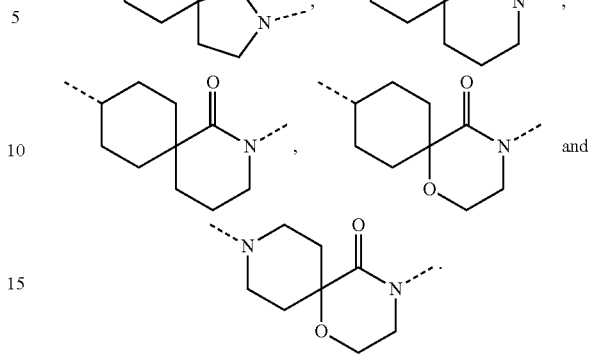
14. The compound or the pharmaceutically acceptable salt thereof according to claim 1, which is selected from
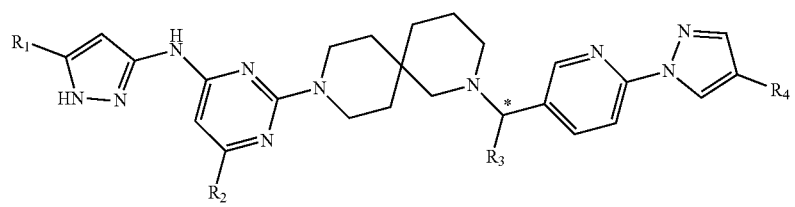
(I-1)
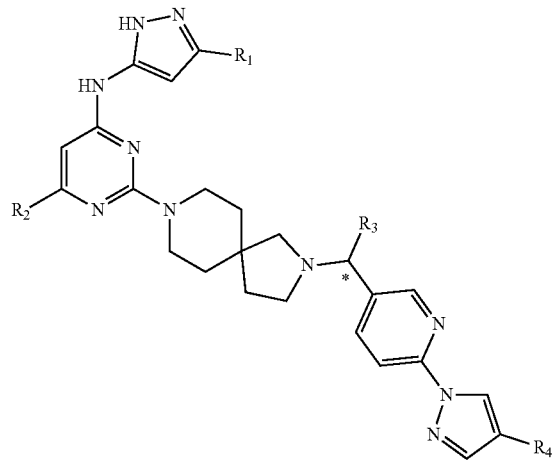
(I-2)
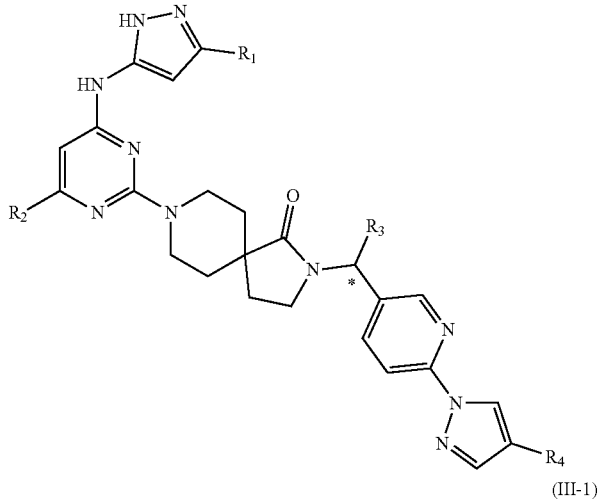
(I-3)
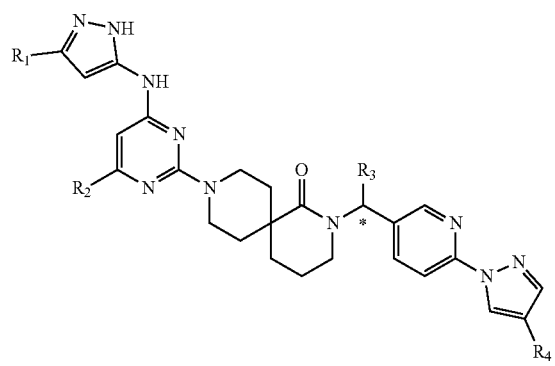
(I-4)
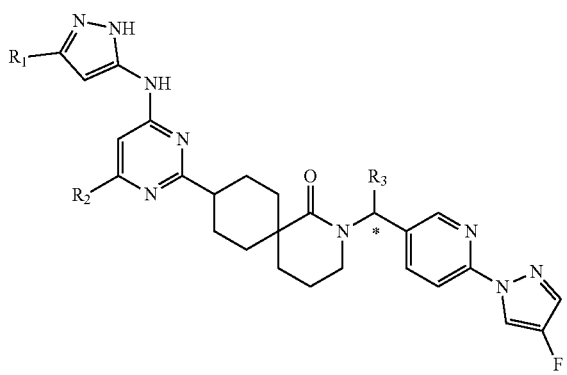
(III-1)

(III-2)
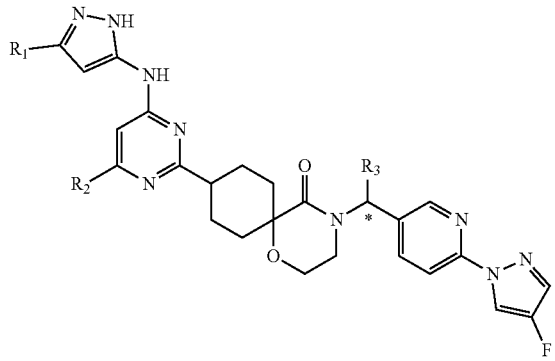
(IV-1)
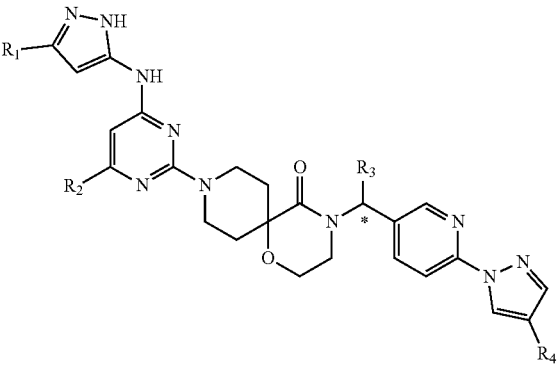
wherein, $R_1$, $R_2$, $R_3$ and $R_4$ are as defined according to claim 1;
a carbon atom with "*" is a chiral carbon atom, which is present in a form of single enantiomer or in an enriched enantiomeric form.
15. A compound or a pharmaceutically acceptable salt thereof, which is selected from:
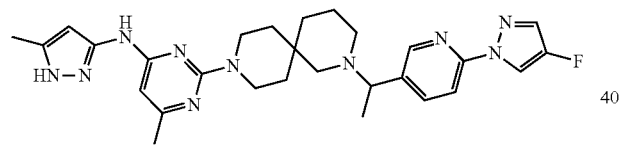
-continued
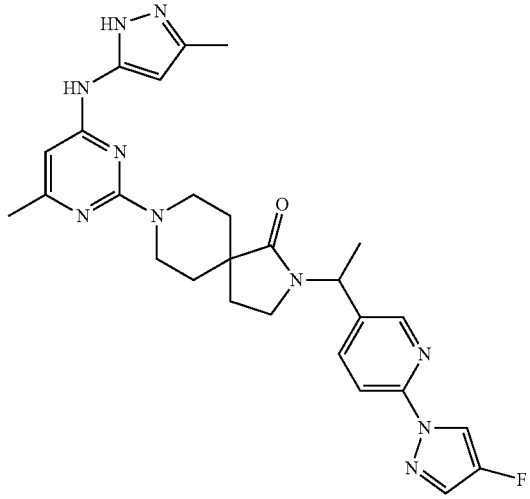
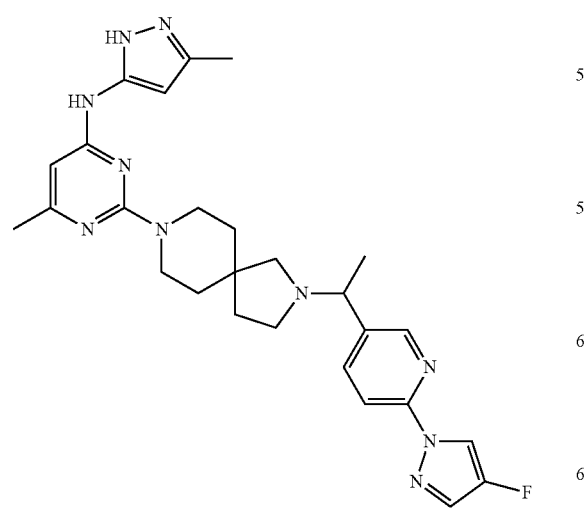
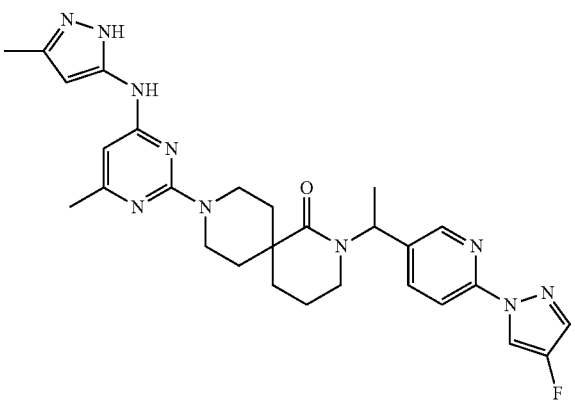

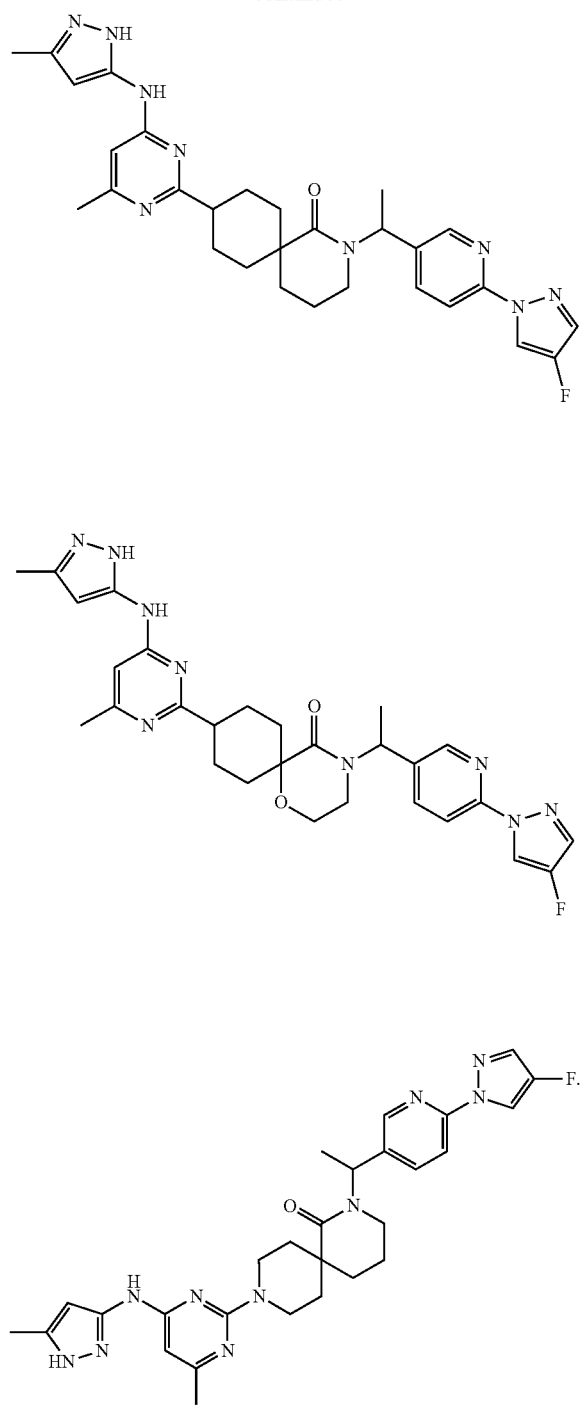
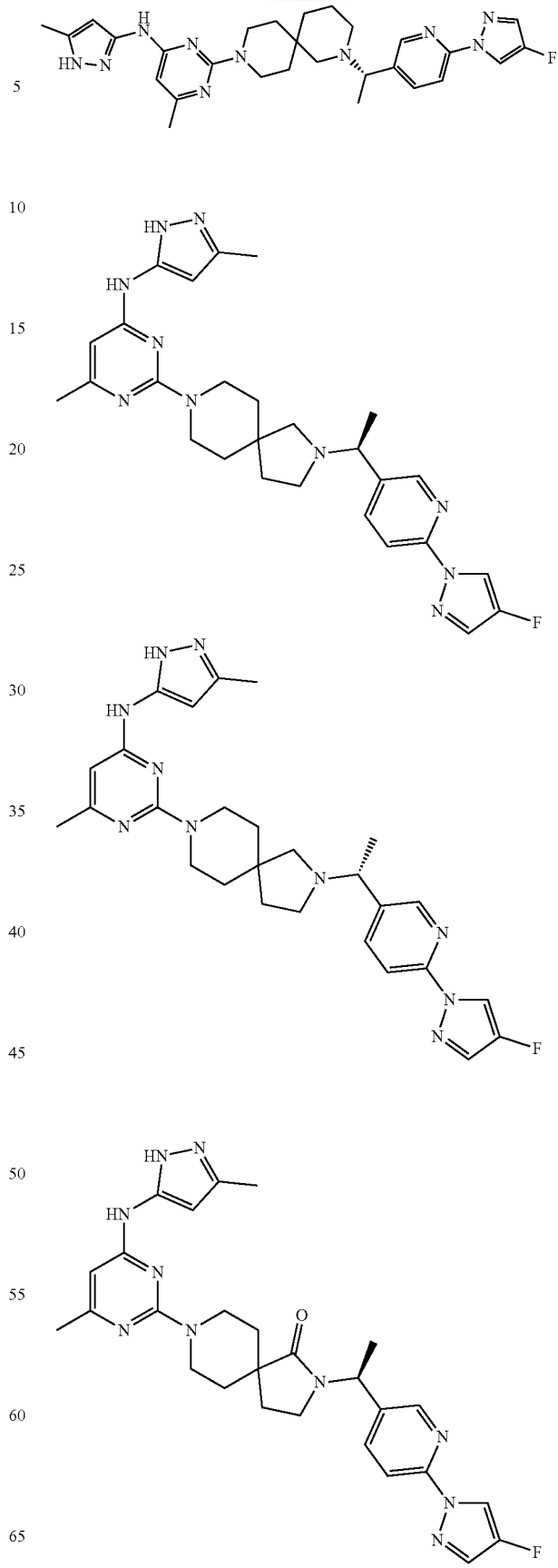
16. The compound or the pharmaceutically acceptable salt thereof according to claim 15, which is selected from
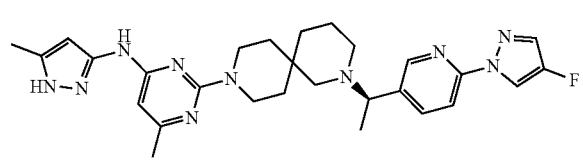

75
-continued
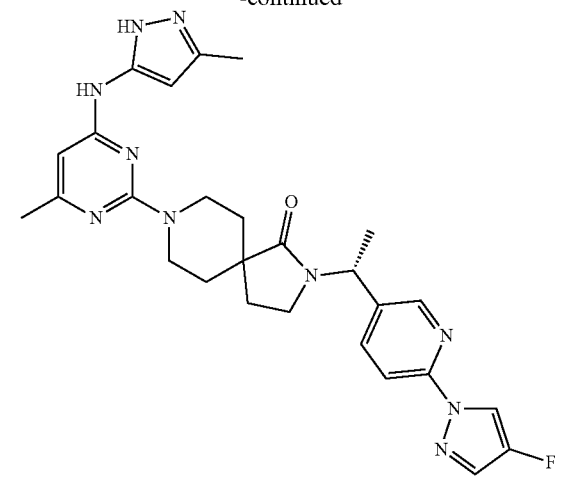
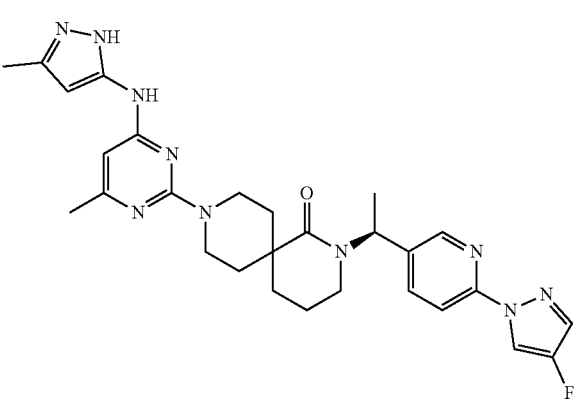
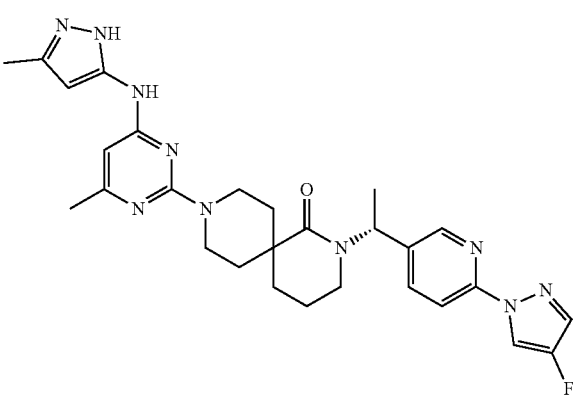
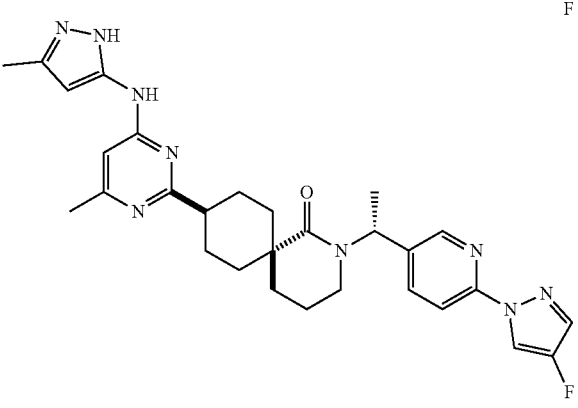
76
-continued
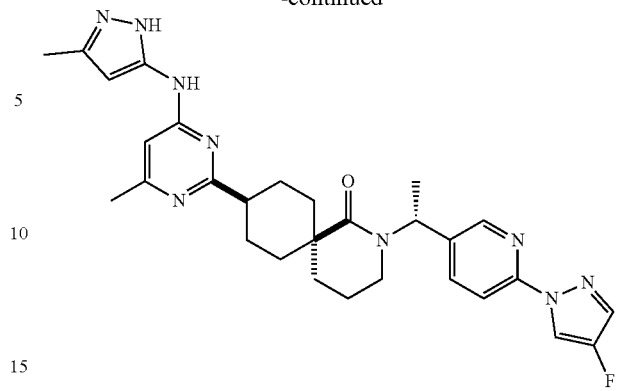
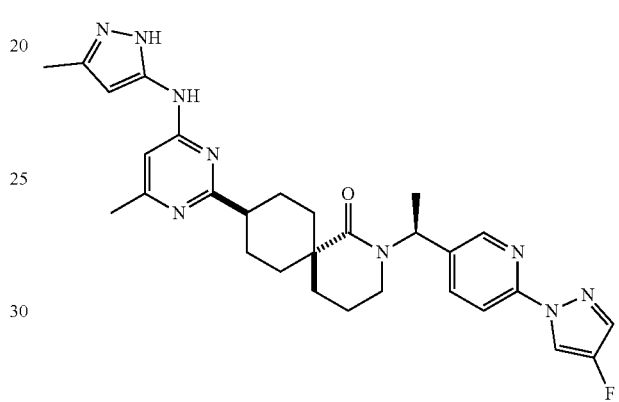
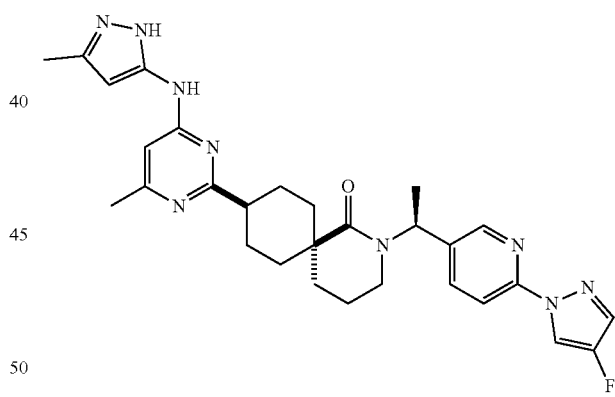
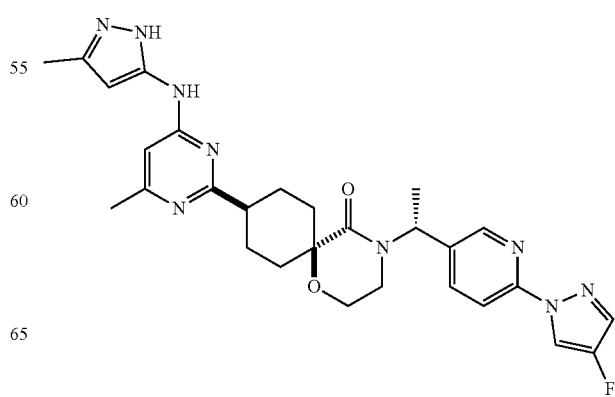

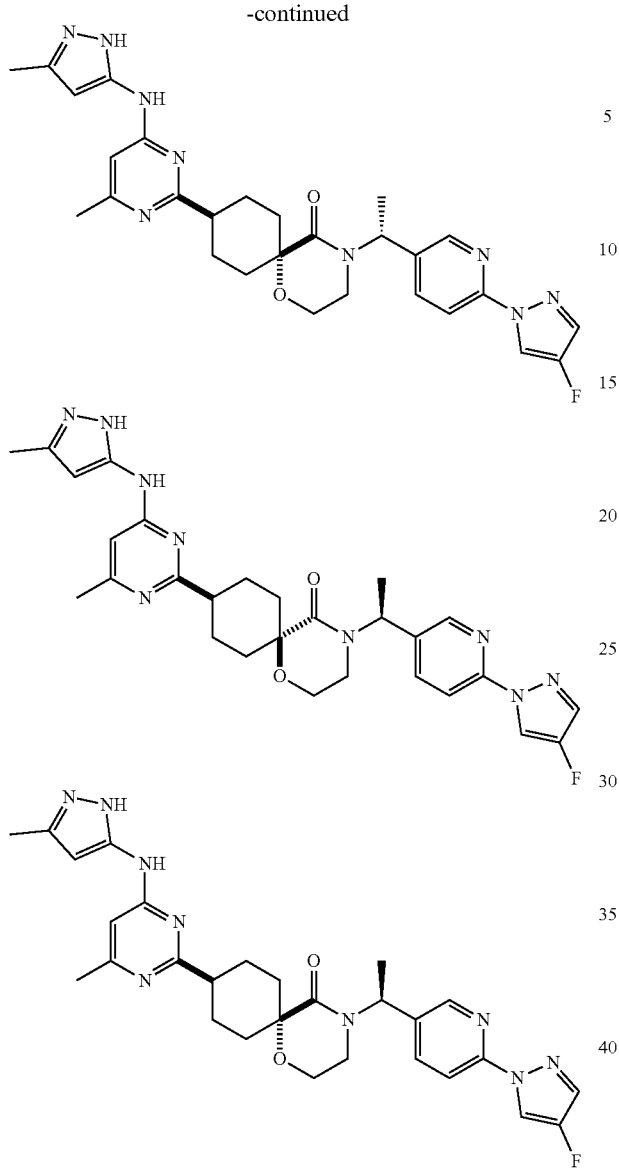

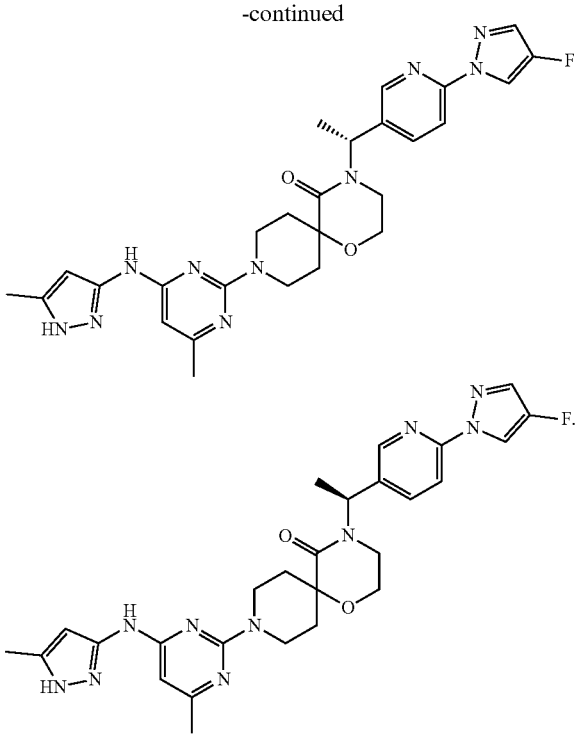

17. A pharmaceutical composition, comprising a therapeutically effective amount of the compound or the pharmaceutically acceptable salt thereof according to claim 1 as an active ingredient and a pharmaceutically acceptable carrier.

18. A pharmaceutical composition, comprising a therapeutically effective amount of the compound or the pharmaceutically acceptable salt thereof according to claim 15 as an active ingredient and a pharmaceutically acceptable carrier.

19. A RET kinase inhibitor, comprising a therapeutically effective amount of the compound or the pharmaceutically acceptable salt thereof according to claim 1.

* * * * *